(12) United States Patent
Chung et al.

(10) Patent No.: US 10,308,945 B2
(45) Date of Patent: Jun. 4, 2019

(54) BACTERIUM PRODUCING MONOPHOSPHORYL LIPID A AND METHOD OF PRODUCING MONOPHOSPHORYL LIPID A BY USING BACTERIUM

(71) Applicant: KOREA INSTITUTE OF SCIENCE AND TECHNOLOGY, Seoul (KR)

(72) Inventors: Hak Suk Chung, Seoul (KR); Eun Gyeong Yang, Seoul (KR); Dohyeon Hwang, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 30 days.

(21) Appl. No.: 15/378,681

(22) Filed: Dec. 14, 2016

(65) Prior Publication Data
US 2017/0191071 A1    Jul. 6, 2017

(30) Foreign Application Priority Data
Jan. 6, 2016    (KR) .................. 10-2016-0001708

(51) Int. Cl.
| | |
|---|---|
| C12P 19/12 | (2006.01) |
| C12N 15/70 | (2006.01) |
| C12N 9/10 | (2006.01) |
| C12N 9/16 | (2006.01) |
| C12N 15/52 | (2006.01) |
| C12N 15/74 | (2006.01) |

(52) U.S. Cl.
CPC ............ *C12N 15/70* (2013.01); *C12N 9/1029* (2013.01); *C12N 9/16* (2013.01); *C12N 15/52* (2013.01); *C12N 15/74* (2013.01); *C12P 19/12* (2013.01)

(58) Field of Classification Search
None
See application file for complete search history.

(56) References Cited

U.S. PATENT DOCUMENTS

2010/0272758 A1    10/2010    Woodard et al.
2013/0230555 A1    9/2013     Trent et al.

FOREIGN PATENT DOCUMENTS

| CN | 102399736 A | 4/2012 |
|---|---|---|
| CN | 104844665 A | 8/2015 |

OTHER PUBLICATIONS

Chen et al. Biotechnol. Lett. 33:1013-1019, 2011 (Year: 2011).*
Reynolds et al. Biochemistry 48:9627-9640, 2009 (Year: 2009).*
Zhou et al. Cell Mol Life Sci 63:2260-2290, 2006 (Year: 2006).*
Kozak, M. Gene 234:187-208, 1999 (Year: 1999).*
Wang et al., "Purification and Characterization of Lipopolysaccharides" in "Endotoxins: Structure, Function and Recognition. Subcellular Biochemistry", vol. 53, Springer, Dordrecht, 2010 (Year: 2010).*
KEGG Entry K12977 2018, 1 page (Year: 2018).*
KEGG Entry K02517 2018, 1 page (Year: 2018).*
Six et al., Biochemistry 47:862-867, 2008 (Year: 2008).*
GenBank Accession No. AAC74138, Aug. 2014, 3 pages (Year: 2014).*
Tran et al. J. Bacteriol. 188:4531-4541, 2006 (Year: 2006).*
GenBank Accession No. WP_000713906 May 2013, 1 page (Year: 2013).*
Karbarz et al., J. Biol. Chem. 284, 414-425, 2009 (Year: 2009).*
Yaning Han et al., Construction of Monophosphoryl Lipid A Producing *Escherichia coli* Mutants and Comparison of Immuno-Stimulatory Activities of Their Lipopolysaccharides, Mar. Drugs, Jan. 21, 2013, pp. 363-376, vol. 11.
Communication from Korean Intellectual Property Office for Non-Final Office Action dated Nov. 18, 2016 of the Korean patent application No. 10-2016-0001708, which corresponds to the present application.
Biwen Wang et al, Immuno-Stimulatory Activity of *Escherichia coli* Mutants Producing Kdo2-Monophosphoryl-Lipid A on Kdo2-Pentaacyl-Monophosphoryl-Lipid A , PLOS ONE 10(12) , Dec. 28, 2015, pp. 1-15.
Meredith Timothy C. et al. Redefining the requisite lipopolysaccharide structure in *Escherihcia coli*, ACS Chemical Biology, Jan. 24, 2006, pp. 33-42,vol. 1, No. 1.
Extended European search report dated Apr. 15, 2019 of the European Patent application No. 16884011.4, which corresponds to the above-identified application.

* cited by examiner

*Primary Examiner* — David Steadman
(74) *Attorney, Agent, or Firm* — Goldilocks Zone IP Law

(57)    ABSTRACT

A bacterium producing monophosphoryl lipid A (MLA) comprising a genetic modification that increases expression of a gene encoding LpxE polypeptide and a method of producing MLA are provided. According to the present invention, MLA may be produced in a simple manner without acid hydrolysis and/or base hydrolysis.

14 Claims, 8 Drawing Sheets

Specification includes a Sequence Listing.

US 10,308,945 B2

BACTERIUM PRODUCING MONOPHOSPHORYL LIPID A AND METHOD OF PRODUCING MONOPHOSPHORYL LIPID A BY USING BACTERIUM

CROSS-REFERENCE TO RELATED APPLICATION

This application claims the benefit of Korean Patent Application No. 10-2016-0001708, filed on Jan. 6, 2016, in the Korean Intellectual Property Office, the disclosure of which is incorporated herein in its entirety by reference.

BACKGROUND

1. Field

One or more embodiments relate to a bacterium that produces monophosphoryl lipid A (MLA), and a method of producing MLA by using the bacterium.

2. Description of the Related Art

Lipopolysaccharides (LPS) are one of the components of the outer membrane surrounding peptidoglycan of Gram-negative bacteria. LPS are molecules containing lipid A and a variety of polysaccharides conjugated with the lipid A by a covalent bond. Among the components of LPS, Lipid A, which is also known as endotoxin, is held responsible for the toxicity of Gram-negative bacteria.

Lipid A is a very potent stimulant of the immune system, activating cells (for example, monocytes or macrophages) at picogram per milliliter quantitites. Lipid A, derivatives of lipid A, or varients of lipid A can be used as, for example, components of vaccines such as adjuvants. Monophosphoryl lipid A (MLA) is used as adjuvants and used for allergen-specific immunotherapy and immunotherapy of cancer, or also effective in prevention and treatment of dementia. Furthermore, among MLA, hexa-acylated-monophosphoryl lipid A (hexa-acylated MLA), penta-acylated-monophosphoryl lipid A (penta-acylated MLA), and 3-O-desacyl-4'-monophosphoryl lipid A (3D-MLA) are effective in the above-mentioned use. Lipid A is a lipid component found in the membrane of Gram-negative bacteria, such as *Escherichia coli*. Lipid A found in the membrane conjugates to sugars, such as 2-keto-3-deoxy-D-manno-octulosonate (Kdo). Therefore, in order to obtain lipid A in a free form, it should be isolated from the other components of LPS. For example, LPS can be extracted from bacterial membranes, heated in the presence of acids so as to remove Kdo, and a 1-phosphate group, thereby obtaining Lipid A; or MLA can be synthesized by chemical processing. However, these methods have drawbacks in that they are complicated in steps of the processes, with a low yield.

Therefore, there is a need to develop a method of producing MLA and derivatives thereof, which is simpler than the conventional methods, without acid hydrolysis.

SUMMARY

Provided is a bacterium that produces monophosphoryl lipid A (MLA).

Provided is a method of producing MLA.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
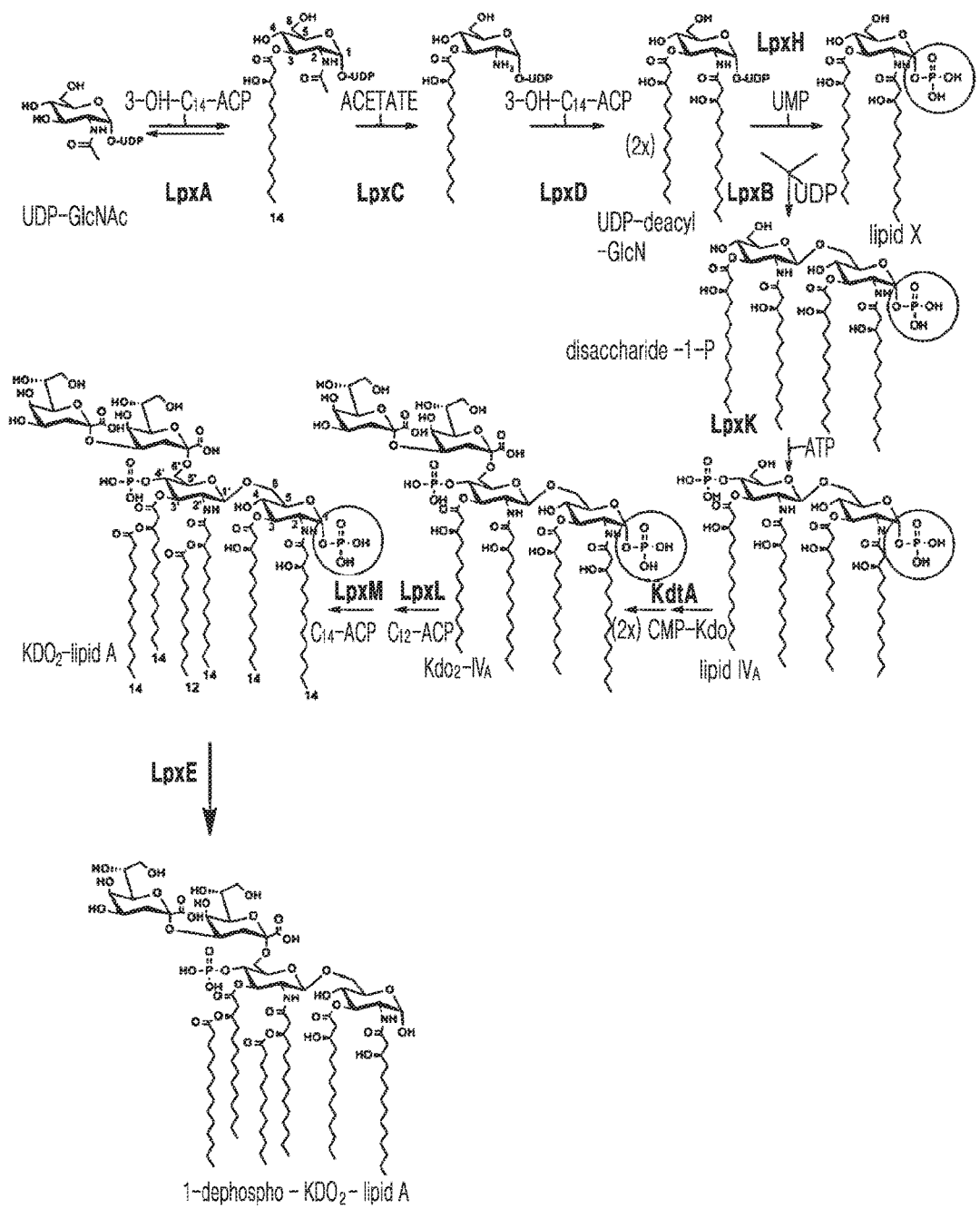
FIG. 1 is a schematic diagram of biosynthetic pathway of 1-dephospho-Kdo$_2$-lipid A in a bacterium.

The term "increase expression" used herein refers to a detectable increase in expression product of a certain gene, for example, mRNA or a protein encoded by the gene in a cell. The term "parent bacterial cell" used herein refers to a bacterial cell of the same type that does not have a particular genetic modification. When a wild-type cell is used in the genetic modification, the parent bacterial cell may be a "wild-type" cell. For example, bacterium comprising a genetic modification that increases expression of a gene may have higher level of expression product than that of parent bacterial cell by about 5% or more, about 10% or more, about 15% or more, about 20% or more, about 30% or more, about 40% or more, about 50% or more, about 60% or more, about 70% or more, about 80% or more, about 90% or more, about 95% or more, or about 100% or more. Increase in expression product in a cell may be verified by any methods known in the art. The level of expression product may be determined by measuring activities or quantities of the expression product such as mRNA or protein.

The term "decrease expression" used herein refers to a detectable decrease in expression product of a certain gene, for example, mRNA or a protein encoded by the gene in a cell. The term "parent bacterial cell" used herein refers to a bacterial cell of the same type that does not have a particular genetic modification. When a wild-type cell is used in the genetic modification, the parent bacterial cell may be a "wild-type" cell. For example, bacterium comprising a genetic modification that decreases expression of a gene may have lower level of expression product than that of parent bacterial cell by about 5% or more, about 10% or more, about 15% or more, about 20% or more, about 30% or more, about 40% or more, about 50% or more, about 60% or more, about 70% or more, about 80% or more, about 90% or more, about 95% or more, or about 100% or more.

Decrease in expression product in a cell may be verified by any methods known in the art. The level of expression product may be determined by measuring activities or quantities of the expression product such as mRNA or protein.

The terms "disruption", "disrupted", and the like used herein refer to reduced expression of a given gene due to a genetic modification. Disruption can be caused by a genetic modification that completely nullifies expression of a referenced gene (hereinafter, referred to as "inactivation" of a gene.). Disruption also includes a genetic modification that causes expression of a gene at decreased levels without completely nullifying expression (hereinafter referred to as "attenuation" of a gene.). Expression, in this sense, refers to transcription of a gene product as well as translation of an active gene product. Thus, inactivation includes a case in which a gene is not transcribed or translated, such that the product of a gene is not expressed, and a case in which, although a gene is transcribed and translated, the gene product is not functional. Similarly, attenuation includes a case in which transcription and/or translation of a gene is reduced, as well as a case in which transcription and/or translation is not reduced, but the gene product has a lower activity level. Herein, the term "a functional product of a gene" means that the gene product (e.g., protein or enzyme) has a biochemical or physiologic function (for example, enzyme activity). The disruption of the gene includes a functional disruption of the gene, wherein the biochemical or physiologic function in a genetically modified cell is reduced or completely nullified in comparison to a parent or wild-type cell.

Genetic modification includes a modification that introduces a polynucleotide encoding a polypeptide into a cell; a modification that substitutes, adds (i.e., inserts), or deletes one or more nucleotides of the genetic material of a parent cell, including a chemical modification (exposure to a chemical) resulting in a change to the genetic material of a parent cell. Genetic modification includes a heterologous or homologous modification of referenced species. Genetic modification includes a modification of a coding region for polypeptides. Genetic modification also includes a modification of non-coding regulatory regions that change expression of a gene or function of an operon. Non-coding regions include 5'-non-coding sequence (5' of a coding sequence) and 3'-non-coding sequence (3' of a coding sequence).

The disruption of a gene may be achieved by a genetic engineering method, such as homologous recombination, directed mutagenesis, or directed molecular evolution. When a cell includes a plurality of identical genes or 2 or more paralogs of a gene, one or more genes may be disrupted. For example, the genetic modification may involve transforming a cell with a vector including the sequence of a gene, and then culturing the cell to cause a homologous recombination of the exogenous nucleic acid and an endogenous gene of the cell, thereby disrupting the endogenous gene. The cell that has undergone homologous recombination can be screened out (selected) by using a selective marker.

The "gene" used herein refers to a nucleic acid fragment that encodes a particular protein, which may optionally include at least one regulatory sequence, such as a 5'-non-coding sequence and a 3'-non-coding sequence (3' and 5' in reference to the position relative to the coding sequence).

The term "sequence identity" of a nucleic acid or polypeptide used herein refers to a degree of identity of nucleotides or amino acid residues of two corresponding sequences over a particular region measured after the sequences are aligned to be matched with each other as much as possible. The sequence identity is a value that is measured by comparing two optimally aligned corresponding sequences of a particular comparable region, wherein in the comparable region, a part of the sequence may be added or deleted compared to a reference sequence. In some embodiments, a percentage of the sequence identity may be calculated by comparing two optimally aligned corresponding sequences in an entire comparable region, determining the number of locations where an amino acid or a nucleic acid is identical in the two sequences to obtain the number of matched locations, dividing the number of the matched locations by the total number (that is, a range size) of all locations within a comparable range, and multiplying the result by 100 to obtain a percentage of the sequence identity. The percent of the sequence identity may be determined by using known sequence comparison programs, examples of which include BLASTN and BLASTP (NCBI), CLC Main Workbench (CLC bio.), MegAlign™ (DNASTAR Inc).

In identifying polypeptides or polynucleotides of different species that may have identical or similar function or activity, similarity in sequence identity may be used. For example, similar sequences may have a sequence identity of 50% or more, 55% or more, 60% or more, 65% or more, 70% or more, 75% or more, 80% or more, 85% or more, 90% or more, 95% or more, 96% or more, 97% or more, 98% or more, 99% or more, or 100%.

The term "exogenous" and the like used herein refers to a referenced molecule (e.g., nucleic acid) or referenced activity that has been introduced into a host cell. A nucleic acid may be exogenously introduced into a host in any suitable manner. For example, a nucleic acid can be introduced into a host cell and inserted into a host chromosome, or the nucleic acid can be introduced into the host as non-chromosomal genetic material, such as an expression vector (e.g., a plasmid) that does not integrate into the host chromosome. A nucleic acid encoding a protein should be introduced in an expressionable form (i.e., so that the nucleic acid can be transcribed and translated). The exogenous gene may include a homologous gene, i.e., an identical gene with the endogenous gene, or a heterologous gene.

An aspect provides a bacterium that produces monophosphoryl lipid A (MLA) comprising a genetic modification that increases expression of a gene encoding LpxE polypeptide as compared to a parent bacterial cell. The bacterium may have enhanced ability to produce MLA. The bacterium may be genetically engineered on or a recombinant one.

The lipid A consists of glucosamine disaccharide with attached acyl chains, and normally contains one phosphate group on each glucosamine. Two disaccharides may linked by $\beta(1\rightarrow6)$ linkage. The acyl chain may be directly attached to hydroxyl residue selected from the group of hydroxyl residue at C-2, C-2', C-3 and C-3' positions of glucosamine disaccharide. The acyl chain may have hydroxyl residue, for example at C-3 position thereof and additional acyl chain may be attached to hydroxyl residue located in the acyl chain. Each of the acyl chain attached may have identical or different. The lipid A may contain 2, 3, 4, 5, 6, or 7 acyl chains. The acyl chain may have 8 to 30 carbon atoms. For example, the acyl chain may have 8, 9, 10, 11, 12, 13, 14, 15, 16, 17, 18, 19, 20, 21 or greater, 25 or greater, or 30 or greater carbons in length. The lipid A moiety of *Escherichia coli* consists of a hexa-acylated bis-1,4'-phosphorylated glucosamine disaccharide, which has (R)-3-hydroxymyristyl residues at C-2, C-2', C-3, and C-3'. Both of the primary (3)-hydroxyacyl chains in the distal glucosamine moiety are esterified with lauric and myristic acids, and the primary hydroxyl at the C-6 position is linked to the polysaccharide through a dimeric 3-deoxy-D-manno-oct-2-ulosonic acid (KDO) carbohydrate moiety. The lipid A of *N. meningitidis* is hexa-acylated in a symmetrical fashion whereas enteric bacteria have an asymmetrically hexa-acylated lipid A Also, a number of the fatty acids of *N. meningitidis* are shorter compared to those of *E. coli*.

The MLA refers to a monophosphoryl lipid A in which only one phosphate group is joined to C-1 or C-4' position of glucosamine disaccharide. The MLA may be tri-acylated MLA, tetra-acylated MLA, penta-acylated MLA, hexa-acylated MLA, or hepta-acylated MLA. For example, the MLA may be 1-dephospho-lipid A, 1-dephospho-penta-acylated lipid A, 3-O-deacyl-4'-MLA (3D-MLA), or a combination thereof. In this case, lipid A may be lipid A of *E. coli*. The 3D-MLA is also known as 1-dephospho-3-O-deacyl-lipid A.

The MLA may not include 2-keto-3-deoxy-D-manno-octulosonate (Kdo). Kdo is a component of lipopolysaccharides (LPS).

The MLA may be present in a membrane, for example, in an outer membrane, of a living bacterium.

The bacterium may include increased copy number of gene encoding LpxE polypeptide. The bacterium may include at least one of an exogenous polynucleotide encoding LpxE polypeptide.

The LpxE polypeptide belongs to EC 3.1.3.-. The LpxE belongs to the family of lipid phosphate phosphatases. The LpxE may contain a tripartite active site and six transmembrane helices. A lipid phosphate phosphatase is a hydrolase, specifically acting to phosphoric monoester bonds, which may remove a phosphate group from a lipid containing a phosphate group. The LpxE may be phosphate phosphatase specifically dephosphorylating the 1-position. The LpxE polypeptide may be an LpxE polypeptide of bacterium selected from the group consisting of *Aquifex* genus bacterium, *Helicobacter* genus bacterium, *Francisella* genus bacterium, *Bordetella* genus bacterium, *Brucella* genus bacterium, *Rhizobium* genus bacterium, *Mesorhizobium* genus bacterium, *Legionella* genus bacterium, *Agrobacterium* genus bacterium, *Chlorobium* genus bacterium, *Rhodospirillum* genus bacterium, *Magnetospirillum* genus bacterium, *Chlorobaculum* genus bacterium, *Pelodictyon* genus bacterium, *Pseudovibro* genus bacterium, *Phaeospirillum* genus bacterium, *Syntrophobacter* genus bacterium, *Bradyrhizobium* genus bacterium, *Porphyromonas* genus bacterium, *Ralstonia* genus bacterium, *Limnohabitans* genus bacterium, and *Thermodesulfobacterium* genus bacterium. The *Aquifex* genus bacterium may include *Aquifex aeolicus* or *Aquifex pyrophilus*. *Aquifex* genus bacterium are thermophilic bacterium, which may grow best at a temperature ranging from about 85° C. to 95° C. The *Aquifex* genus bacterium may be *Aquifex aeolicus*. The *Helicobacter* genus bacterium may be *Helicobacter pylori*. For example, the LpxE polypeptide may be an LpxE polypeptide derived from *Aquifex aeolicus* (AaLpxE) or an LpxE polypeptide derived from *Helicobacter pylori* (HpLpxE). The LpxE polypeptide may be a polypeptide having about 99%, about 97%, about 95%, about 90%, about 80%, about 70%, about 60%, about 50%, about 40%, about 30%, about 20%, or about 10% or more sequence identity to the amino acid sequence of SEQ ID NO: 9 or SEQ ID NO: 17. The LpxE polypeptide may be encoded by a nucleic acid sequence of SEQ ID NO: 10 or SEQ ID NO: 16; or by a polynucleotide including about 99%, about 97%, about 95%, about 90%, about 80%, about 70%, about 60%, about 50%, about 40%, about 30%, about 20%, or about 10% identity to the nucleic acid sequence of SEQ ID NO: 10 or SEQ ID NO: 16.

The bacterium may further include a genetic modification that increases expression of a gene encoding LpxL polypeptide, a gene encoding LpxM polypeptide, or a combination thereof as compared to a parent bacterial cell.

The bacterium may include increased copy number of gene encoding LpxL polypeptide, gene encoding LpxM polypeptide, or a combination thereof. The bacterium may include an exogenous polynucleotide encoding LpxL polypeptide, an exogenous polynucleotide encoding LpxL polypeptide, or a combination thereof.

The LpxL polypeptide may belong to EC 2.3.1.241. The LpxL polypeptide is a lipid A biosynthesis lauroyltransferase, which catalyzes the transfer of laurate from lauroyl-acyl carrier protein (ACP) to $Kdo_2$-lipid IVA to form $Kdo_2$-(lauroyl)-lipid IVA. The LpxL polypeptide may be an LpxL polypeptide of bacterium selected from the group consisting of *Escherichia* genus bacterium, *Shigella* genus bacterium, *Salmonella* genus bacterium, *Campylobacter* genus bacterium, *Neisseria* genus bacterium, *Haemophilus* genus bacterium, *Aeromonas* genus bacterium, *Francisella* genus bacterium, *Yersinia* genus bacterium, *Klebsiella* genus bacterium, *Bordetella* genus bacterium, *Legionella* genus bacterium, *Corynebacterium* genus bacterium, *Citrobacter* genus bacterium, *Chlamydia* genus bacterium, *Brucella* genus bacterium, *Pseudomonas* genus bacterium, *Bacteroides* genus bacterium, *Prevotella* genus bacterium, *Helicobacter* genus bacterium, *Burkholderia* genus bacterium, *Porphyromonas, Rhizobium* genus bacterium, *Mesorhizobium* genus bacterium, *Serratia* genus bacterium, *Acinetobacter* genus bacterium, *Shewanella* genus bacterium, *Xenorhabdus* genus bacterium, *Photobacterium* genus bacterium, *Lysobacter* genus bacterium, *Enterobacter* genus bacterium, and *Vibrio* genus bacterium. For example, the LpxL polypeptide may be an LpxL polypeptide of *Escherichia coli* (EcLpxL). The LpxL polypeptide may be a polypeptide that includes an amino acid sequence of SEQ ID NO: 1; or a polypeptide having about 99%, about 97%, about 95%, about 90%, about 80%, about 70%, about 60%, about 50%, about 40%, about 30%, about 20%, or about 10% or more sequence identity to the amino acid sequence of SEQ ID NO: 1. The LpxL polypeptide may be encoded by a nucleic acid sequence of SEQ ID NO: 2; or by a polynucleotide having about 99%, about 97%, about 95%, about 90%, about 80%, about 70%, about 60%, about 50%, about 40%, about 30%, about 20%, or about 10% or more sequence identity to the nucleic acid sequence of SEQ ID NO: 2.

The LpxM polypeptide may belong to EC 2.3.1.243. The LpxM polypeptide is a lipid A biosynthesis myristoyltransferase, which catalyzes the transfer of myristate from myristoyl-acyl carrier protein to $Kdo_2$-lauroyl-lipid IVA to form $Kdo_2$-lipid A. The LpxM polypeptide may be an LpxM polypeptide of a bacterium selected from the group consisting of *Escherichia* genus bacterium, *Shigella* genus bacterium, *Salmonella* genus bacterium, *Campylobacter* genus bacterium, *Neisseria* genus bacterium, *Haemophilus* genus bacterium, *Aeromonas* genus bacterium, *Francisella* genus bacterium, *Yersinia* genus bacterium, *Klebsiella* genus bacterium, *Bordetella* genus bacterium, *Legionella* genus bacterium, *Corynebacterium* genus bacterium, *Citrobacter* genus bacterium, *Chlamydia* genus bacterium, *Brucella* genus bacterium, *Pseudomonas* genus bacterium, *Bacteroides* genus bacterium, *Prevotella* genus bacterium, *Helicobacter* genus bacterium, *Burkholderia* genus bacterium, *Porphyromonas* genus bacterium, *Rhizobium* genus bacterium, *Mesorhizobium* genus bacterium, *Serratia* genus bacterium, *Acinetobacter* genus bacterium, *Shewanella* genus bacterium, *Xenorhabdus* genus bacterium, *Photobacterium* genus bacterium, *Lysobacter* genus bacterium, *Enterobacter* genus bacterium, and *Vibrio* genus bacterium. For example, the LpxM polypeptide may be an LpxM polypeptide of *Escherichia coli* (EcLpxM). The LpxM polypeptide may be a polypeptide that includes an amino acid sequence of SEQ ID NO: 5; or a polypeptide having about 99%, about 97%, about 95%, about 90%, about 80%, about 70%, about 60%, about 50%, about 40%, about 30%, about 20%, or about 10% or more sequence identity to the amino acid sequence of SEQ ID NO: 5. The LpxM polypeptide may be encoded by a nucleic acid sequence of SEQ ID NO: 6; or by a polynucleotide having about 99%, about 97%, about 95%, about 90%, about 80%, about 70%, about 60%, about 50%, about 40%, about 30%, about 20%, or about 10% or more sequence identity to the nucleic acid sequence of SEQ ID NO: 6.

The term "bacterium" as used herein refers to a prokaryotic bacterium. The bacterium may be Gram-negative bacteria. The Gram-negative bacteria may not retain the crystal violet stain used in the Gram staining method. The cell membranes of Gram-negative bacteria are composed of double membranes of an inner membrane and an outer membrane with a thin peptidoglycan layer. The bacterium may be selected from the group consisting of *Escherichia* genus bacterium, *Aquifex* genus bacterium, *Shigella* genus bacterium, *Salmonella* genus bacterium, *Campylobacter* genus bacterium, *Neisseria* genus bacterium, *Haemophilus* genus bacterium, *Aeromonas* genus bacterium, *Francisella* genus bacterium, *Yersinia* genus bacterium, *Klebsiella* genus bacterium, *Bordetella* genus bacterium, *Legionella* genus bacterium, *Corynebacterium* genus bacterium, *Citrobacter* genus bacterium, *Chlamydia* genus bacterium, *Brucella* genus bacterium, *Pseudomonas* genus bacterium, *Helicobacter* genus bacterium, *Burkholderia* genus bacterium, *Agrobacterium* genus bacterium, *Chlorobium* genus bacterium, *Rhodospirillum* genus bacterium, *Magnetospirillum* genus bacterium, *Chlorobaculum* genus bacterium, *Pelodictyon* genus bacterium, *Pseudovibro* genus bacterium, *Phaeospirillum* genus bacterium, *Syntrophobacter* genus bacterium, *Bradyrhizobium* genus bacterium, *Porphyromonas* genus bacterium, *Rhizobium* genus bacterium, *Mesorhizobium* genus bacterium, *Vibrio* genus bacterium, *Ralstonia* genus bacterium, *Limnohabitans* genus bacterium, and *Thermodesulfobacterium* genus bacterium. The bacterium may be, for example, *Escherichia coli*.

The bacterium may further include a genetic modification that decreases expression of polynucleotide that encodes a polypeptide involved in Kdo biosynthetic pathway. The polypeptide involved in Kdo biosynthetic pathway may be a polypeptide selected from a group consisting of KdtA, KdsB, KdsC, KdsA, GutQ, KpsF, KpsU and KdsD polypeptide. The KdtA also refers to WaaA. In the bacterium, the following genes may be disrupted: a gene encoding KdtA polypeptide, a gene encoding KdsB polypeptide, a gene encoding KdsC polypeptide, a gene encoding KdsA polypeptide, a gene encoding GutQ polypeptide, a gene encoding KpsF polypeptide, a gene encoding KpsU polypeptide, a gene encoding KdsD polypeptide, or a combination thereof. In the bacterium the following genes may be disrupted: a gene encoding LpxT polypeptide, a gene encoding PagP polypeptide, a gene encoding KdtA polypeptide, or a combination thereof.

The LpxT polypeptide may belong to EC 2.7.4.29. The LpxT polypeptide may be an inner membrane protein. The LpxT polypeptide is a phosphotransferase, which catalyzes the transfer of a 1-phosphate group from undecaprenyl pyrophosphate to lipid A to form lipid A 1-pyrophosphate. The LpxT polypeptide may be an LpxT polypeptide of bacterium selected from the group consisting of *Escherichia* genus bacterium, *Shigella* genus bacterium, *Salmonella* genus bacterium, *Campylobacter* genus bacterium, *Neisseria* genus bacterium, *Haemophilus* genus bacterium, *Aeromonas* genus bacterium, *Francisella* genus bacterium, *Yersinia* genus bacterium, *Klebsiella* genus bacterium, *Bordetella* genus bacterium, *Legionella* genus bacterium, *Corynebacterium* genus bacterium, *Citrobacter* genus bacterium, *Chlamydia* genus bacterium, *Brucella* genus bacterium, *Pseudomonas* genus bacterium, *Helicobacter* genus bacterium, *Burkholderia* genus bacterium, *Porphyromonas* genus bacterium, *Rhizobium* genus bacterium, *Mesorhizobium* genus bacterium, and *Vibrio* genus bacterium. For example, the LpxT polypeptide may be an LpxT polypeptide of *Escherichia coli* (EcLpxT). The LpxT polypeptide may be a polypeptide that includes an amino acid sequence of SEQ ID NO: 20; or a polypeptide having about 99%, about 97%, about 95%, about 90%, about 80%, about 70%, about 60%, about 50%, about 40%, about 30%, about 20%, or about 10% or more sequence identity to the amino acid sequence of SEQ ID NO: 20. The LpxT polypeptide may be encoded by a nucleic acid sequence of SEQ ID NO: 21; or by a polynucleotide having about 99%, about 97%, about 95%, about 90%, about 80%, about 70%, about 60%, about 50%, about 40%, about 30%, about 20%, or about 10% or more sequence identity to the nucleic acid sequence of SEQ ID NO: 21.

The PagP polypeptide may belong to EC 2.3.1.251. The PagP polypeptide may be a lipid A palmitoyltransferase, which is required for biosynthesis of hepta-acylated lipid A species containing palmitate. The PagP polypeptide catalyzes the transfer of a palmitate chain (16:0) from the sn-1 position of a glycerophospholipid to the free hydroxyl group of the (R)-3-hydroxymyristate chain at position 2 of lipid A. The PagP polypeptide may be a PagP polypeptide of bacterium selected from the group consisting of *Escherichia* genus bacterium, *Shigella* genus bacterium, *Salmonella* genus bacterium, *Campylobacter* genus bacterium, *Neisseria* genus bacterium, *Haemophilus* genus bacterium, *Aeromonas* genus bacterium, *Francisella* genus bacterium, *Yersinia* genus bacterium, *Klebsiella* genus bacterium, *Bordetella* genus bacterium, *Legionella* genus bacterium, *Corynebacterium* genus bacterium, *Citrobacter* genus bacterium, *Chlamydia* genus bacterium, *Brucella* genus bacterium, *Pseudomonas* genus bacterium, *Helicobacter* genus bacterium, *Burkholderia* genus bacterium, *Porphyromonas* genus bacterium, *Rhizobium* genus bacterium, *Mesorhizobium* genus bacterium, and *Vibrio* genus bacterium. For example, the PagP polypeptide may be a PagP polypeptide of *Escherichia coli* (EcPagP). The PagP polypeptide may be a polypeptide that includes an amino acid sequence of SEQ ID NO: 26; or a polypeptide having about 99%, about 97%, about 95%, about 90%, about 80%, about 70%, about 60%, about 50%, about 40%, about 30%, about 20%, or about 10% or more sequence identity to the amino acid sequence of SEQ ID NO: 26. The PagP polypeptide may be encoded by a nucleic acid sequence of SEQ ID NO: 27; or by a polynucleotide having about 99%, about 97%, about 95%, about 90 about 80%, about 70%, about 60%, about 50%, about 40%, about 30%, about 20%, or about 10% or more sequence identity to the nucleic acid sequence of SEQ ID NO: 27.

The KdtA polypeptide may belong to EC 2.4.99.12., EC 2.4.99.13., EC 2.4.99.14., and/or EC 2.4.99.15. The KdtA (or WaaA) polypeptide may be an enzyme that catalyzes the transfer of Kdo to lipid IVA. For example, the KdtA polypeptide may be a KdtA polypeptide of *Escherichia coli* (EcKdtA). EcKdtA may catalyze the transfer of two Kdo to lipid IVA. The KdtA polypeptide may be a polypeptide that includes an amino acid sequence of SEQ ID NO: 22; or a polypeptide having about 99%, about 97%, about 95%, about 90%, about 80%, about 70%, about 60%, about 50%, about 40%, about 30%, about 20%, or about 10% or more sequence identity to the amino acid sequence of SEQ ID NO: 22. The KdtA polypeptide may be encoded by a nucleic acid sequence of SEQ ID NO: 23; or by a polynucleotide having about 99%, about 97%, about 95%, about 90%, about 80%, about 70%, about 60%, about 50%, about 40%, about 30%, about 20%, or about 10% or more sequence identity to the nucleic acid sequence of SEQ ID NO: 23.

Another aspect provides method of producing MLA that includes culturing the bacterium described above to obtain a culture; and isolating MLA from the culture.

The method may include culturing bacterium that produces monophosphoryl lipid A (MLA) comprising a genetic modification that increases expression of a gene encoding LpxE polypeptide as compared to a parent bacterial cell to obtain a culture.

The LpxE polypeptide, MLA, and bacterium are the same as those described herein.

The culturing may be performed using a method known in the art. The type of culture solution, the culturing temperature, and the culturing conditions may be those that are known in the art. The culturing temperature may be for example, about 10° C. to about 43° C., about 20° C. to about 43° C., about 20° C. to about 40° C., about 25° C. to about 43° C., about 25° C. to about 35° C., about 27° C. to about 33° C., about 10° C. to about 15° C., about 15° C. to about 20° C., about 20° C. to about 25° C., about 25° C. to about 30° C., about 30° C. to about 33° C., about 33° C. to about 37° C., about 37° C. to about 40° C., or about 40° C. to about 43° C. The bacterium may be cultured in a batch, fed-batch culture, or continuous mode. The culturing may be performed in stationary, or shaking condition. The culturing period may be, for example, about 1 hour to about 1 week, about 3 hours to about 6 days, about 6 hours to about 5 days, about 9 hours to about 4 days, about 12 hours to about 3 days, about 18 hours to about 2 days, about 1 day, or overnight. The culture medium may include antibiotics. Examples of the antibiotics may include kanamycin, ampicillin, chloramphenicol, or a combination thereof.

The method may include isolating MLA from the culture. The isolating may include isolating MLA from the bacterial cell. The isolating may include isolating the bacterial cell from the culture. Isolating the bacterial cell from a culture may be performed by using a method known in the art. For example, the bacterium may be isolated from a culture by centrifugation. The isolated bacterium may be washed with a buffer solution.

The method may include isolating MLA from the bacterium.

The MLA may be separated from lipid of the bacterium. The method of separating lipid may be one that is known in the art. MLA may be obtained by a physical or chemical method. The physical method may be, for example, repeated ultrasound pulses or repeated freeze-thaw. The chemical method may be extraction by using an organic solvent. Examples of the organic solvent may include chloroform, phenol, petroleum ether, dichloromethane, methanol, hexane, isopropyl alcohol, ethyl acetate, acetonitrile, ethanol, or a combination thereof. Examples of the method of extracting lipid may be a Bligh and Dyer lipid extraction protocol (see Bligh, E. G. and Dyer, W. J., Can. J. Biochem. Physiol., 1959, vol. 37, p. 911-917). The method may further include purifying MLA in lipid. The method may not include hydrolysis step to remove Kdo moiety since the obtained lipid A may be a free form, i.e., not conjugated to Kdo moiety.

The MLA may include 1-dephospho-lipid A, 1-dephospho-tetra-acylated lipid A, 1-dephospho-penta-acylated lipid A, 3D-MLA, or a combination thereof.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

Hereinafter, the present invention will be described in more detail with reference to Examples. However, these Examples are for illustrative purposes only, and the invention is not intended to be limited by these Examples.

Example 1. Preparation of Vector Including Polynucleotide that Encodes *Escherichia coli* LpxL and *Escherichia coli* LpxM 1.1. Preparation of pWSK29-EcLpxLEcLpxM In order to obtain a polynucleotide that encodes *Escherichia coli* LpxL polypeptides, from the *Escherichia coli* W3110 genome (GenBank Accession No. NC_000918.1, ATCC), a polynucleotide (GenBank Accession No. AP009048.1 (c1118159.1117239, SEQ ID NO: 2), which encodes an EcLpxL polypeptide (GenBank Accession No. BAA35852.1, SEQ ID NO: 1) including a ribosome binding site (RBS), was amplified by a first polymerase chain reaction (PCR) using a pair of primers shown below (see FIG. 2A).

LpxL forward primer P1: SEQ ID NO: 3
LpxL reverse primer P2: SEQ ID NO: 4

Figure 2A:
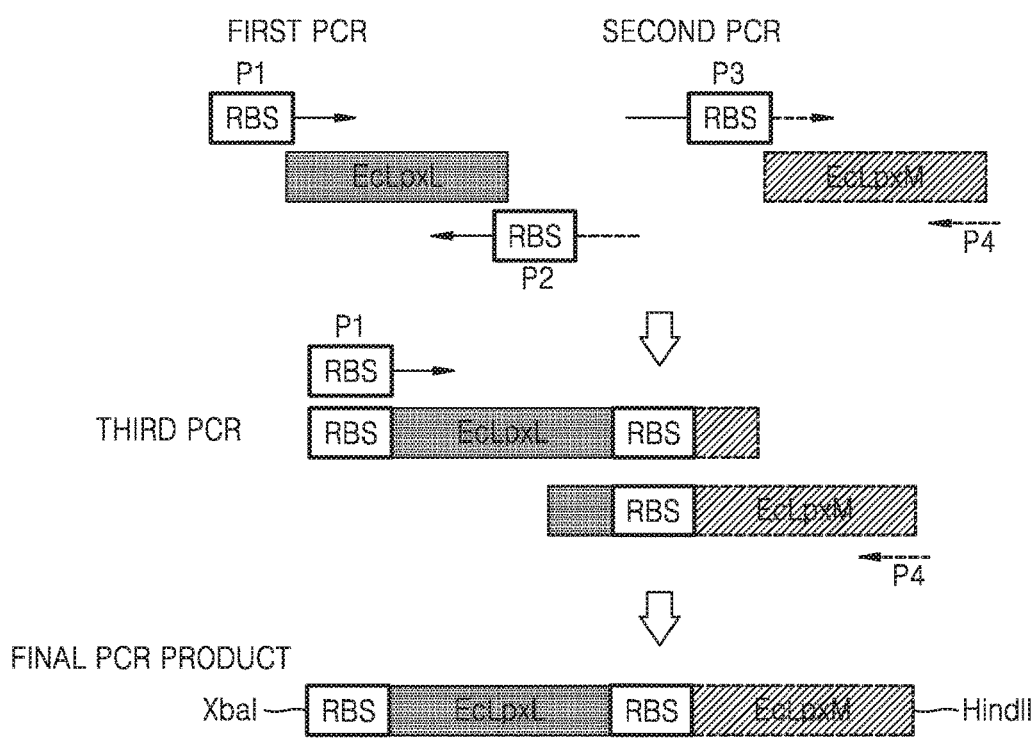
FIG. 2A is a schematic diagram of a method of producing PCR products including EcLpxL and EcLpxM.

In order to obtain a polynucleotide that encodes *Escherichia coli* LpxM polypeptides, from the *Escherichia coli* W3110 genome, a polynucleotide (GenBank Accession No. AP009048.1 (c1941907.1940936, SEQ ID NO: 6), which encodes an EcLpxM polypeptide (GenBank Accession No. BAA15663.1, SEQ ID NO: 5) including an RBS, was amplified by a second PCR using a pair of primers shown below (see FIG. 2A).

LpxM forward primer P3: SEQ ID NO: 7
LpxM reverse primer P4: SEQ ID NO: 8

An EcLpxLEcLpxM polynucleotide, which is a fusion of the EcLpxL polynucleotide and the EcLpxM polynucleotide, was amplified by a third PCR using the LpxL forward primer P1 and the LpxM reverse primer P4 and the EcLpxL polynucleotide obtained from the first PCR and the EcLpxM polynucleotide obtained from the second PCR as a template.

The PCRs were performed using a KOD hot start DNA polymerase (Novagen) in a T3000 thermocycler (Biometra).

The amplified products were purified using a DokDo-Prep PCR purification kit (ELPIS), and the purified products were introduced into at XbaI and HindIII restriction site of a pWSK29 plasmid (Wang, R. F., and Kushner, S. R., Gene (1991), vol. 100, p. 195-199). The cloned plasmid was transformed into *Escherichia coli* DH5α by electroporation, and then selected on an LB-ampicillin plate. The cloned plasmid was named as pWSK29-EcLpxLEcLpxM.

1.2. Preparation of pBAD33.1-AaLpxE 1.2.1. Preparation of pET21-AaLpxE

In order to obtain a polynucleotide that encodes *Aquifex aeolicus* LpxE (AaLpxE) polypeptides, from the *Aquifex aeolicus* VF5 genome (GenBank Accession No. NC_000918.1, ATCC), a polynucleotide (GenBank Accession No. NC_000918.1:1199317 . . . 1199841, SEQ ID NO: 10), which encodes AaLpxE polypeptide (GenBank Accession No. NP_214169.1, SEQ ID NO: 9), was amplified by using a pair of primers shown below.

AaLpxE forward primer: SEQ ID NO: 11
AaLpxE reverse primer: SEQ ID NO: 12

As described in 1.1, the PCR was performed, and the amplified products were purified. The purified products were introduced into at NdeI and XhoI restriction enzyme stie of pET21a plasmid (Novagen). The cloned plasmid was transformed into *E. coli* DH5a and selected as described in 1.1. The cloned plasmid was named as pET21-AaLpxE.

1.2.2. Preparation of pBAD33.1-AaLpxE

A polynucleotide that encodes AaLpxE was amplified using the pET21-AaLpxE prepared in 1.2.1 as a template and a pair of primers shown below.

AaLpxE forward primer: SEQ ID NO: 13
AaLpxE reverse primer: SEQ ID NO: 14

The PCR was performed using a KOD hot start DNA polymerase (Novagen) in a T3000 thermocycler (Biometra).

As described in 1.1, the PCR was performed, and the amplified products were purified. The purified products were cloned into pBAD33.1 at NdeI and HindIII restriction enzyme site (Chung, H. S., and Raetz, C. R., Biochemistry (2010), vol. 49 (19), p. 4126-4137). The cloned plasmid, as described in 1.1, was transformed into *E. coli* and then selected. The cloned plasmid was named as pBAD33.1-AaLpxE as an expression vector.

1.2.3. Preparation of pBAD33.1-HpLpxE

In hp0021, which is a *Helicobacter pylori* LpxE (HpLpxE) gene, for the deletion of a HindIII restriction enzyme recognition site sequence, a polynucleotide sequence (SEQ ID NO: 16), which has Ser codon AGC at a position corresponding to 17 Ser residue and differs from that TCG of 17 polynucleotide sequence (SEQ ID NO: 15), was synthesized by integrated DNATechnologies (mBiotech, ROK). A polynucleotide that encodes HpLpxE amino acid sequences (SEQ ID NO: 17) was amplified using the synthesized DNA as a template and a pair of primers shown below.

Forward primer: SEQ ID NO: 18
Reverse primer: SEQ ID NO: 19

The PCR was performed using a KOD hot start DNA polymerase (Novagen) in a T3000 thermocycler (Biometra).

As described in 1.1, the PCR was performed, and the amplified products were purified. The purified products were cloned into pBAD33.1 at XbaI and HindIII restriction enzyme site (Chung, H. S., and Raetz, C. R., Biochemistry (2010), vol. 49(19), p. 4126-4137). The cloned plasmid, as described in 1.1, was transformed into *Escherichia coli* and then selected. The cloned plasmid was named as pBAD33.1-HpLpxE as an expression vector.

Example 2. Preparation of *Escherichia coli* KHSC003 (pWSK29-EcLpxLEcLpxM, kdtA::kan, ΔlpxT, ΔpagP, W3110) Strains 2.1. Preparation of *Escherichia coli* in which lpxT Gene is Removed from Genome Into *Escherichia coli* strain W3110, lpxT::kan, in which a kanamycin cassette is inserted into a lpxT gene (SEQ ID NO: 21) in the *Escherichia coli* genome that encodes an LpxT polypeptide (SEQ ID NO: 20), pCP20 plasmid (Kirill A. Datsenko, and Barry L. Wanner PNAS (2000), vol. 97, p. 6640-6645), as described in 1.1., was transformed and then selected on an LB-ampicillin solid medium. The selected *Escherichia coli* was inoculated on an LB solid medium, and selected at a temperature of 42° C., thereby preparing an *Escherichia coli* strain from which lpxT and the kanamycin cassette were removed, i.e., ΔlpxT, W3110 (step 1 in FIG. 26).

Figure 2B:
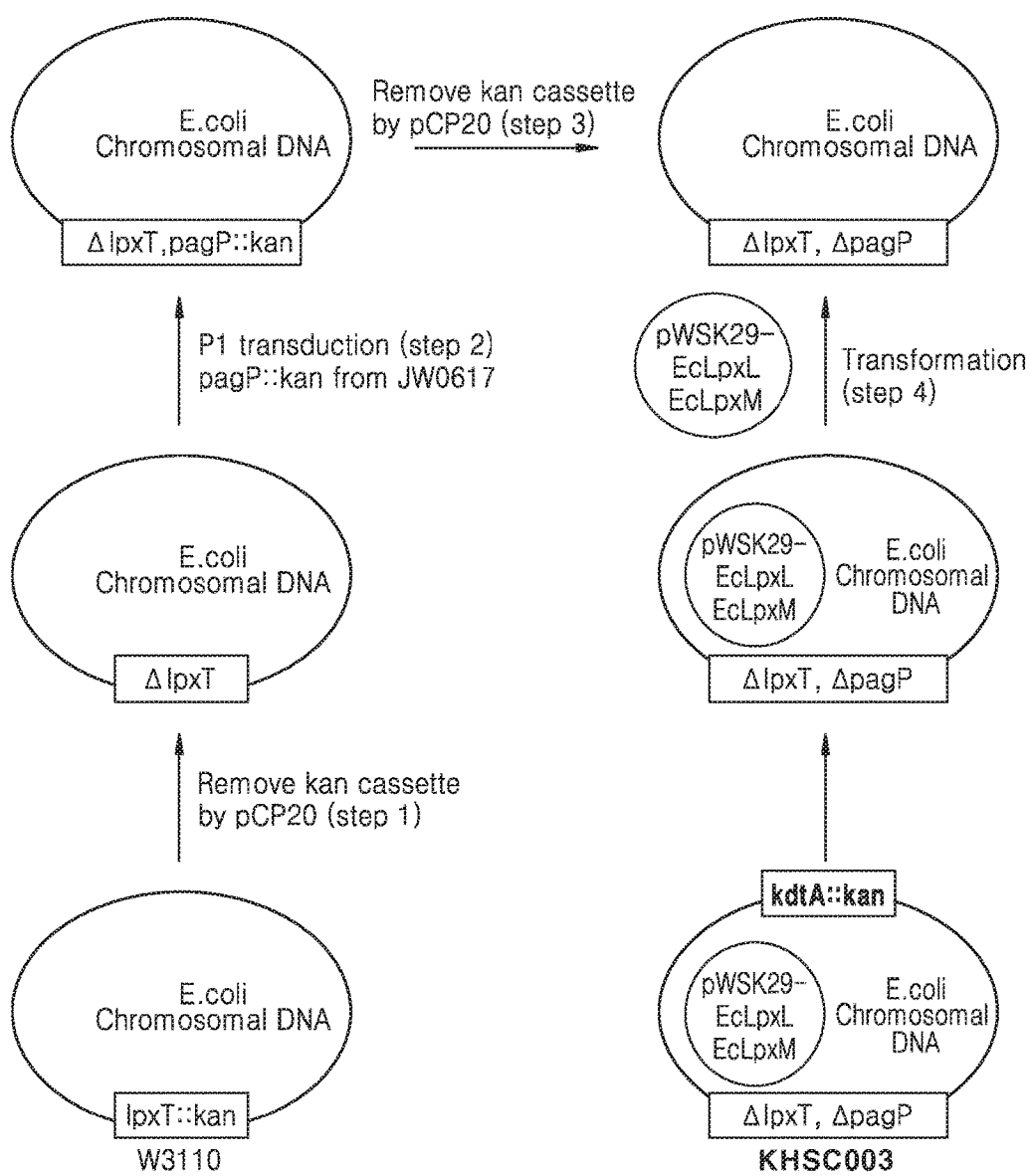
FIG. 2B is a schematic diagram of a method of producing an *Escherichia coli* strain KHSC003.

2.2. Preparation of *Escherichia coli* in which pagP and lpxT Genes are Removed from Genome From an *Escherichia coli* strain (JW0617 (pagP::kan)), in which a kanamycin cassette is inserted into a pagP gene in the *Escherichia coli* genome, P1 virus was prepared (Current Protocols in Molecular Biology (2007), 1.16.1-1.16.24, Unit 1.16). The P1 virus was transduced into ΔlpxT, W3110 prepared in 2.1, and then selected on an LB-kanamycin solid medium, thus preparing an *Escherichia coli* strain, into which pagP::kan was inserted in place of pagP gene, i.e., ΔlpxT, pagP::kan, W3110 (Current Protocols in Molecular Biology (2007), 1.16.1-1.16.24, Unit 1.16) (step 2 in FIG. 2B). pCP20 plasmid (KiriII A. Datsenko, and Barry L. Wanner, PNAS (2000), vol. 97, p. 6640-6645) was transformed into the ΔlpxT, pagP::kan, W3110, and then selected on an LB-ampicillin solid medium. The selected *Escherichia coli* was inoculated on an LB solid medium, and selected at a temperature of 42° C., thereby preparing an *Escherichia coli* strain from which pagP and the kanamycin cassette were removed, i.e., ΔlpxT, ΔpagP, W3110 (step 3 in FIG. 2B).

2.3. Preparation of *Escherichia coli* pWSK29-EcLpxLEcLpxM, ΔlpxT, ΔpagP, W3110 Strain The pWSK29-EcLpxLEcLpxM plasmid prepared in 1.1 was transformed into ΔlpxT, ΔpagP, W3110 prepared in 2.2 by electroporation. The transformed *Escherichia coli* was selected on an LB-ampicillin solid medium, thus preparing an *Escherichia coli* pWSK29-EcLpxLEcLpxM, ΔlpxT, ΔpagP, W3110 strain (step 4 in FIG. 2B).

2.4. Preparation of *Escherichia coli* KHSC003 Strain

From *Escherichia coli* including pEcKdtA plasmid, in which a kanamycin cassette is inserted into a kdtA gene (SEQ ID NO: 23) that encodes KdtA polypeptides (SEQ ID NO: 22) in an *Escherichia coli* chromosome, that is, HSC1/pEcKdt (Chung, H. S., and Raetz, C. R., Biochemistry (2010), vol. 49 (19), p. 4126-4137), P1 virus was prepared (Current Protocols in Molecular Biology (2007) 1.16.1-1.16.24, Unit 1.16). The P1 virus was transduced into *Escherichia coli* pWSK29-EcLpxLEcLpxM, ΔlpxT, ΔpagP, W3110 strain, prepared in 2.3, and then selected on an LB-kanamycin/ampicillin solid medium (step 5 in FIG. 2B). The selected *Escherichia coli* was named as KHSC003 (pWSK29-EcLpxLEcLpxM, ΔlpxT, ΔpagP, kdtA::kan, W3110).

Example 3. Test of Lipid of *Escherichia coli* into which AaLpxE, HpLpxE, or FnLpxE were Introduced 3.1. Extraction of Lipid from *Escherichia coli* W3110 Transformed with pWSK29-FnLpxE by Acid Hydrolysis For a comparative experiment, an *Escherichia coli* strain W3110 into which pWSK29-FnLpxE was transformed, and an *Escherichia coli* strain W3110 into which pWSK29-FnLpxE was untransformed were prepared.

Specifically, a pWSK29-FnLpxE (Wang, X., Karbarz, M. J., McGrath, S. C., Cotter, R. J., and Raetz, C. R., J Biol Chem (2004), vol. 279 (47), p. 49470-49478) was prepared, which amplifies a polynucleotide (gb|CP000439.11: 414941-415660 *Francisella novicida* U112, SEQ ID NO: 25) that encodes FnLpxE polypeptides (gi|118422929|gb|ABK89319.1, *Francisella novicida* U112 lipid A phosphatase, SEQ ID NO: 24). The prepared pWSK29-FnLpxE was transformed into an *Escherichia coli* strain W3110 by electroporation, and then the transformed *Escherichia coli* was selected on an LB solid medium containing 50 μg/ml of ampicillin. The selected colony was inoculated into an LB liquid medium containing 50 μg/ml of ampicillin, and then cultured overnight at 37° C. The culture solution was inoculated into 200 ml of a fresh LB liquid medium containing 50 μg/ml of ampicillin such that absorbance measured at a wavelength of 600 nm (OD600) was 0.06. The diluted culture solution was cultured at 37° C. until OD600 reached 1.0. Then, the culture solution was centrifuged at a centrifugal force of 4000×g at room temperature for about 20 minutes, thus obtaining a cultured *Escherichia coli* strain W3110.

An untransformed *Escherichia coli* strain W3110 was inoculated into a fresh LB liquid medium, and then cultured overnight at 37° C. The culture solution was diluted with 200 ml of a fresh LB liquid medium such that OD600 was 0.06. The diluted culture solution was cultured at 37° C. until OD600 reached 1.0. Then, the culture solution was centrifuged at a centrifugal force of 4000 g at room temperature for about 20 minutes, thus obtaining a cultured *Escherichia coli* strain W3110. The obtained *Escherichia coli*, pWSK29-FnLpxE/W3110 and W3110, were each washed with 30 ml of phosphate buffered saline (PBS), then resuspended with 8 ml of PBS. 10 ml of chloroform (EMD millipore) and 20 ml of methanol (EMD millipore) were added to the resuspended *Escherichia coli*, and then incubated at room temperature for about 1 hour by shaking the mixture a few times. Subsequently, the incubated mixture was centrifuged at a centrifugal force of 2500×g for about 30 minutes at room temperature. The supernatant of the centrifuged mixture was discarded, and then the pellet was resuspended with 30 ml of a solution of chloroform, methanol, and PBS at a ratio of 1:2:0.8 (v/v). The resuspended mixture was centrifuged at a centrifugal force of 2500×g for about 30 minutes at room temperature, and the supernatant of the centrifuged mixture was discarded. The pellet was washed two more times in the same manner as above and then the supernatant of the centrifuged mixture was discarded. The washed pellet was resuspended with 18 ml of a 12.5 mM sodium acetate solution (pH 4.5, Sigma-Aldrich) and then sonic-irradiated. The sonic-irradiated solution was heated airtight in boiling water at a temperature of 100° C. for about 30 minutes, and then cooled to room temperature. 20 ml of chloroform (EMD millipore) and 20 ml of methanol (EMD millipore) were added to the cooled solution and then fully mixed together with one another, followed by centrifuging the mixture at a centrifugal force of 2500 g for about 20 minutes at room temperature. An organic solvent layer was separated from the centrifuged mixture, and then a pre-equilibrated organic solvent layer was added to the upper aqueous layer so as to extract an organic solvent layer twice. The organic solvent layer was pooled, and then dried in a rotary evaporator to obtain lipid. The obtained lipid was dissolved in 5 ml of a mixture of chloroform and methanol at a ratio of 4:1 (v/v), and then sonic-irradiated in a water bath. The sonic-irradiated lipid was moved to a new test tube, and then the obtained lipid was dried at room temperature under nitrogen gas, followed by storing at −80° C.

3.2. Extraction of Lipid from *Escherichia coli* KHSC003 Transformed with pBDA33.1, pBAD33.1-AaLpxE, or pBAD33.1-HpLpxE The plasmid prepared in 1.2.2, pBAD33.1-AaLpxE or pBAD33.1-HpLpxE, was transformed into *Escherichia coli* KHSC003 prepared in 2.4, and then the lipid of the membrane of *Escherichia coli* was tested. As for a negative control group, *Escherichia coli* KHSC003, into which a vector pBAD33.1 was transformed, was used.

Specifically, the vector pBAD33.1, pBAD33.1-AaLpxE prepared in 1.2.2, or pBAD33.1-HpLpxE prepared in 1.2.3 was transformed into *Escherichia coli* strain KHSC003 prepared in 2.4 by electroporation. The KHSC003 strain containing pBAD33.1-AaLpxE has been deposited in the Korea Research Institute of Bioscience and Biotechnology, which is an international depository authority under the Budapest Treaty as of Nov. 18, 2016 (Accession Number: KCTC 13155BP). The KHSC003 strain containing pBAD33.1-HpLpxE has been deposited in the Korea Research Institute of Bioscience and Biotechnology, which is an international depository authority under the Budapest Treaty as of Nov. 18, 2016 (Accession Number: KCTC 13156BP).

The transformed *Escherichia coli* was inoculated to an LB liquid medium containing 50 μg/ml of ampicillin (EMD millipore) and 30 μg/ml chloramphenicol (Sigma-Aldrich), and then cultured overnight at 30° C. The culture solution was inoculated to 200 ml of an LB liquid medium containing 50 μg/ml of ampicillin, 30 μg/ml of chloramphenicol, and 1 mM of isopropyl 1-thio-β-D-galactoside (IPTG, UBP Bio), and thus the culture solution was diluted such that OD600 was 0.06 to 0.1. The culture solution was cultured until OD600 reached 0.5 to 0.6. The culture solution was centrifuged at room temperature at a centrifugal force of 4000×g for about 20 minutes so as to obtain *Escherichia coli*. The obtained *Escherichia coli* was washed with 30 ml of PBS and then resuspended with 8 ml of PBS. 10 ml of chloroform and 20 ml of methanol were added to the resuspended *Escherichia coli*, and then incubated at room temperature for about 1 hour with shaking a few times. The incubated mixture was centrifuged at a centrifugal force of 2500×g for about 30 minutes at room temperature, thus obtaining the supernatant thereof. 10 ml of chloroform and 10 ml of water were added to the obtained supernatant followed by complete-mixing of the mixture. Then, the mixture was centrifuged at a centrifugal force of 2500×g for about 20 minutes at room temperature. An organic solvent layer was separated from the centrifuged mixture, and then a pre-equilibrated organic solvent layer was added to the upper aqueous layer so as to extract an organic solvent layer twice. The organic solvent layer was pooled, and then dried in a rotary evaporator to obtain lipid. The obtained lipid was dissolved in 5 ml of a solution of chloroform and methanol at a ratio of 4:1 (v/v), and then sonic-irradiated in a water bath. The sonic-irradiated lipid was moved to a new test tube, and then the obtained lipid was dried at room temperature under nitrogen gas, followed by storing at −80° C.

3.3. Thin Layer Chromatography (TLC) Analysis on Lipid

In order to perform TLC, as described in 3.1 or 3.2, lipid was obtained from 200 ml of an *Escherichia coli* culture solution, and one-third of the total obtained lipid was dissolved in 200 μl of a mixture of chloroform and methanol at a ratio of 4:1 (v/v). Subsequently, 5 μl to 15 μl of the mixture was spotted on a 10×10 cm HPTLC plate (EMD Chemicals) and developed in a solvent of chloroform, methanol, water, and ammonium hydroxide (from 30% to 20%) at a ratio of 40:25:4:2 (v/v. The developed plate was then dried, visualized by spraying 10% (v/v) of sulfuric acid (in ethanol) thereto, and then was charred on a hot plate of 300° C. The results of lipid TLC are shown in FIGS. 3A and 3B (In FIG. 3A, Lane 1: lipids obtained by acid hydrolysis of the extracted LPS from *Escherichia coli* W3110, Lane 2: lipids obtained by acid hydrolysis of the extracted LPS from *Escherichia coli* W3110 containing pWSK29-FnLpxE, Lane 3: extracted lipids obtained from *Escherichia coli* KHSC003 containing pBAD33.1, and Lane 4: extracted lipids obtained from *Escherichia coli* KHSC003 containing pBAD33.1-AaLpxE; and in FIG. 3B, Lane 1: lipids obtained by acid hydrolysis of the extracted LPS from *Escherichia coli* W3110, Lane 2: extracted lipids obtained from *Escherichia coli* KHSC003 containing pBAD33.1-HpLpxE, and Lane 3: extracted lipids obtained from *Escherichia coli* KHSC003 containing pBAD33.1).

Figure 3A:
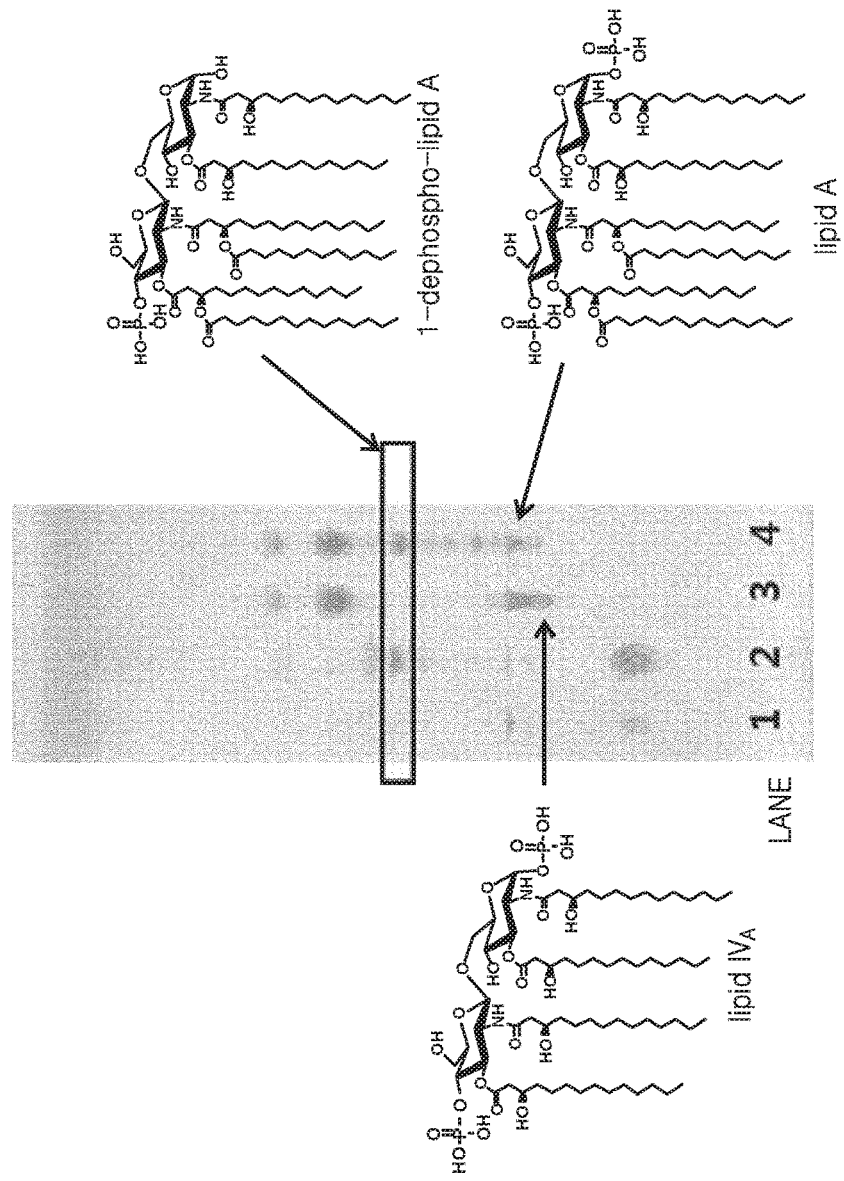
FIGS. 3A and 3B are images illustrating results of thin layer chromatography (TLC) analysis of lipids (In FIG. 3A, Lane 1: lipids obtained by acid hydrolysis of the extracted LPS from *Escherichia coli* W3110, Lane 2: lipids obtained by acid hydrolysis of the extracted LPS from *Escherichia coli* W3110 including pWSK29-FnLpxE, Lane 3: extracted lipids from *Escherichia coli* KHSC003 including pBAD33.1, and Lane 4: extracted lipids from *Escherichia coli* KHSC003 including pBAD33.1-AaLpxE; and in FIG. 3B, Lane 1: lipids obtained by acid hydrolysis of the LPS extracted from *Escherichia coli* W3110, Lane 2: extracted lipids from *Escherichia coli* KHSC003 including pBAD33.1-HpLpxE, and Lane 3: lipids extracted from *Escherichia coli* KHSC003 including pBAD33.1)
Figure 3B:
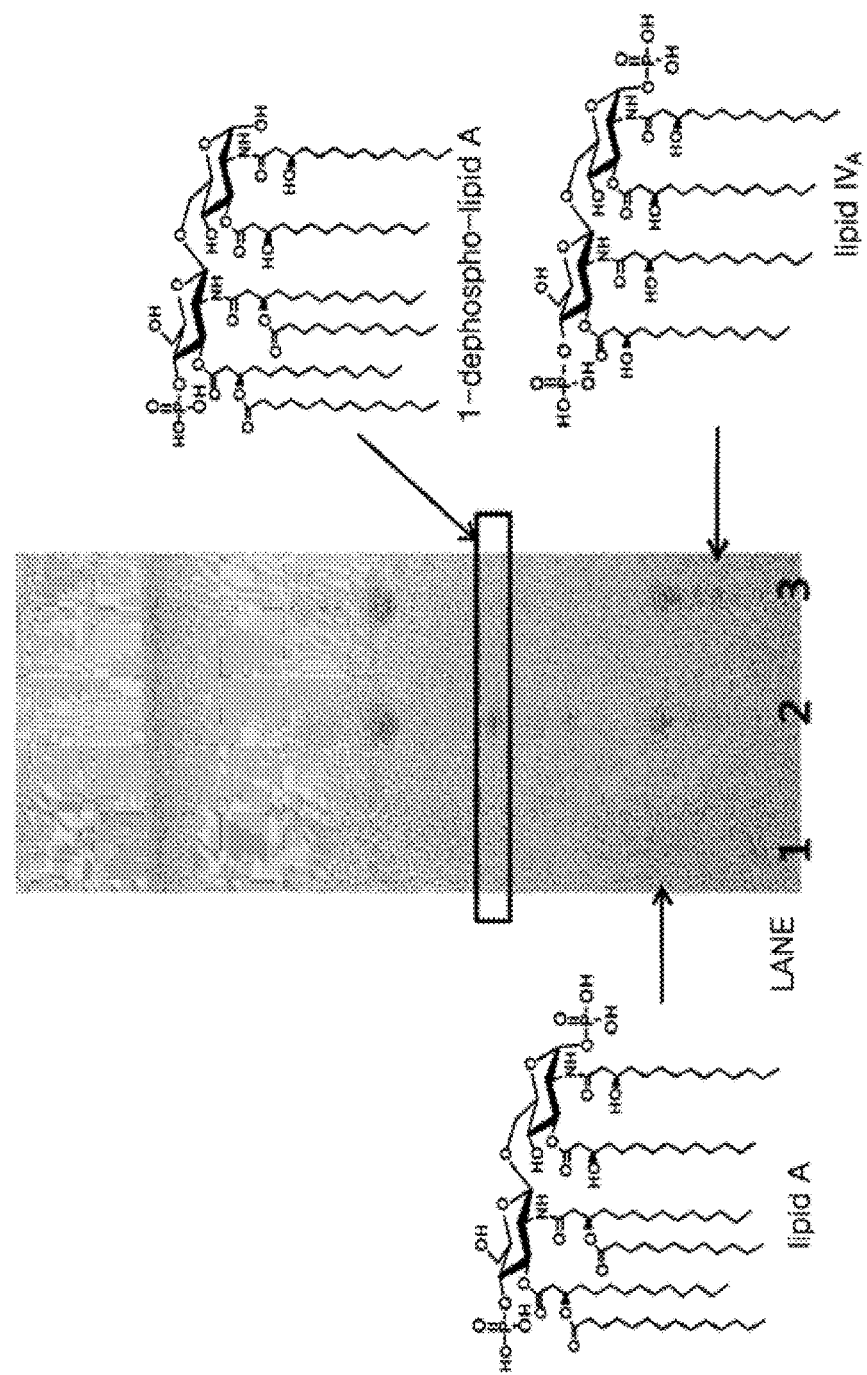

As shown in FIGS. 3A and 3B, lipid A was detected from *Escherichia coli* W3110 that underwent the process of acid hydrolysis (Lane 1 in FIG. 3A), and 1-dephospho-lipid A was detected from *Escherichia coli* W3110 including pWSK29-FnLpxE that underwent the process of acid hydrolysis (Lane 2 in FIG. 3A). In addition, lipid A detected from *Escherichia coli* KHSC003 was detected (Lane 3 in FIG. 3A), and 1-dephospho-lipid A detected from *Escherichia coli* KHSC003 including pBAD33.1-AaLpxE or pBAD33.1-HpLpxE was detected (Lane 4 in FIG. 3A or Lane 2 in FIG. 3B). Therefore, since the membrane of *Escherichia coli* KHSC003 transformed with pBAD33.1-AaLpxE or pBAD33.1-HpLpxE contained 1-dephospho-lipid A, it was found that living *Escherichia coli* containing 1-dephospho-lipid A in the membrane can be obtained. *Escherichia coli* KHSC003 transformed with pBAD33.1-HplLpxE, i.e., pBAD33.1-HplpxE/KHSC003 was internationally deposited on Nov. 23, 2016 with Accession Number KCTC13156BP to Korean Collection for Type Cultures (KCTC) which is an International Depositary Authority according to Budapest Treaty.

3.4. Matrix Assisted Laser Desorption/Ionization Time-of-Flight (MALDI-TOF) Mass Spectrometry on Lipid A and 1-Dephospho-Lipid A The lipid obtained as described in 3.2 was resuspended with a mixture of chloroform and methanol at a ratio of 4:1 (v/v), and the resuspended lipid sample was sent to Korea Basic Science Institute to request MALDI-TOF mass spectrometry.

Figure 4A:
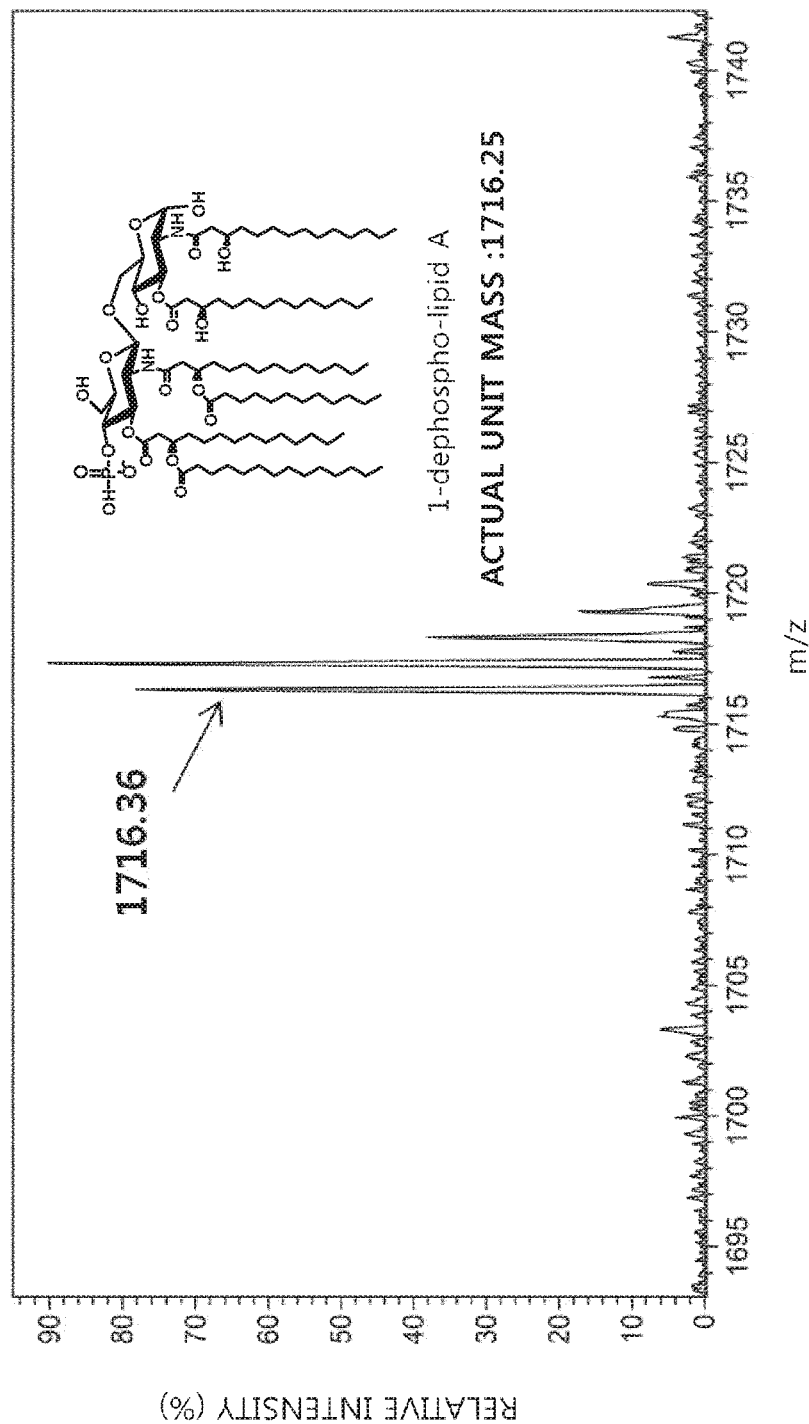
FIG. 4A is a graph illustrating analysis results of matrix assisted laser desorption/ionization time-of-flight (MALDI-TOF) MS on lipid of *Escherichia coli* KHSC003 transformed with pBAD33.1-AaLpxE.

Specifically, a mixture solution of 10 mg/mk of a 2,5-dihydroxybenzoic acid (DHB) solution (Sigma-Aldrich) and acetonitrile (Sigma-Aldrich) at a ratio of 1:4 was used as matrix. 1 µl of the matrix solution was spread on a sample stub, and 1 µl of the resuspended lipid sample was spotted thereon, followed by vacuum-drying. MALDI-TOF mass spectrometry was performed on the lipid sample by using a MALDI-TOF mass spectrometer (Shimadzu Biotech Axima Resonance). The mass spectrometry data was analyzed by using mMass software (www.mmass.org). The analysis results of MALDI-TOF MS are shown in FIG. 4A. The analysis results of MALDI-TOF MS-MS are shown in FIG. 4B (x-axis: mass-to-charge ratio (m/z), y-axis: relative intensity (%)).

Figure 4B:
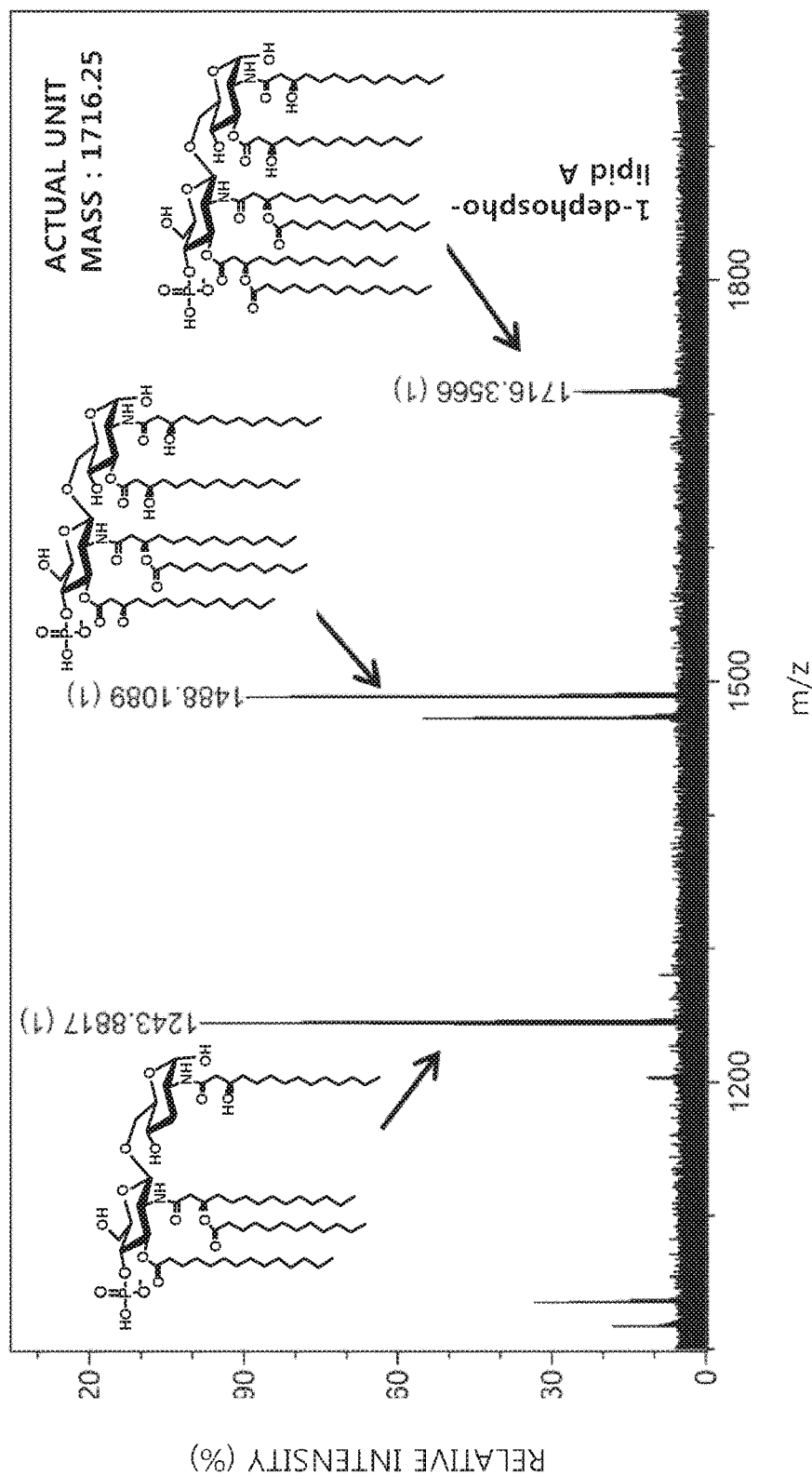
FIG. 4B is a graph illustrating analysis results of MALDI-TOF MS/MS on monophosphoryl-lipid A (m/z: 1716.36) detected in FIG. 4A.
Figure 5:
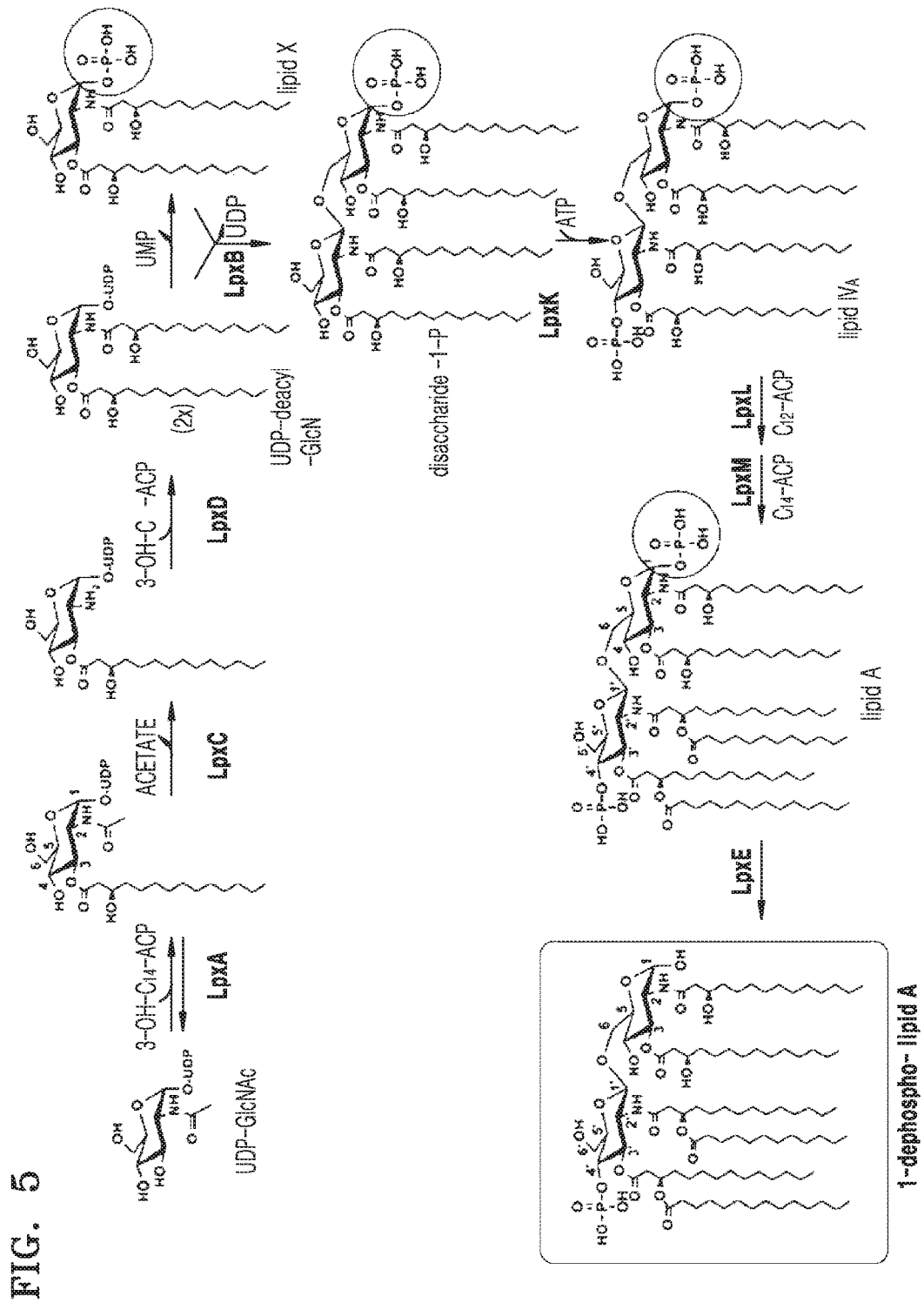
FIG. 5 is a schematic diagram of a process producing MLA in *Escherichia coli* KHSC003 transformed with pBAD33.1-AaLpxE or pBAD33.1-HpLpxE.

As shown in FIGS. 4A and 4B, it was found that from *Escherichia coli* KHSC003 transformed with pBAD33.1-AaLpxE, monophosphoryl lipid A (MLA) not including Kdo, i.e., 1-dephospho-lipid A (the actual unit mass: 1716.25), was detected. Therefore, by the expression of EcLpxM, EcLpxL, and AaLpxE polypeptides in *Escherichia coli*, it was found that living *Escherichia coli* containing 1-dephospho-lipid A in the membrane can be obtained. *Escherichia coli* KHSC003 transformed with pBAD33.1-AaLpxE, i.e., pBAD33.1-AaLpxE/KHSC003 was internationally deposited on Nov. 23, 2016 with Accession Number KCTC13155BP to Korean Collection for Type Cultures (KCTC) which is an International Depositary Authority according to Budapest Treaty.

As described above, when employing bacterium that produces monophosphoryl lipid A (MLA) including an LpxE polypeptide and a method of producing MLA by using the bacterium, according to one or more aspects, MLA may be produced in a simple manner without acid hydrolysis and/or base hydrolysis.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the inventive concept as defined by the following claims.

What is claimed is:

1. A recombinant bacterium that produces monophosphoryl lipid A (MLA) not conjugated to a 2-keto-3-deoxy-D-manno-octulosonate (Kdo) moiety,
   wherein the recombinant bacterium is transformed with at least one exogenous polynucleotide encoding a Lipid A-1 phosphatase (LpxE) polypeptide,
   wherein the recombinant bacterium is modified by 1) transformation with at least one of an exogenous polynucleotide encoding a lipid A biosynthesis lauroyltransferase (LpxL) polypeptide, an exogenous polynucleotide encoding a lipid A biosynthesis myristoyltransferase (LpxM) polypeptide, or a combination thereof, or 2) a genetic modification in a 5'-non-coding sequence or a 3'-non-coding sequence for an endogenous polynucleotide encoding a LpxL polypeptide, an endogenous polynucleotide encoding a LpxM polypeptide, or a combination thereof, wherein the recombinant bacterium has increased expression of the polynucleotide encoding the LpxL polypeptide, the polynucleotide encoding the LpxM polypeptide, or a combination thereof as compared to a corresponding recombinant bacterium without the modification of 1) and 2), and
   wherein the recombinant bacterium has a disruption in a gene encoding a polypeptide involved in Kdo biosynthesis selected from a gene encoding a KdtA polypeptide, a gene encoding a KdsB polypeptide, a gene encoding a KdsC polypeptide, a gene encoding a KdsA polypeptide, a gene encoding a GutQ polypeptide, a gene encoding a KpsF polypeptide, a gene encoding a KpsU polypeptide, a gene encoding a KdsD polypeptide, or a combination thereof.

2. The recombinant bacterium of claim 1, wherein the MLA comprises from 2 acyl chains to 7 acyl chains.

3. The recombinant bacterium of claim 1, wherein the MLA comprises 1-dephospho-lipid A, 1-dephospho-tetra-acylated lipid A, 1-dephospho-penta-acylated lipid A, or a combination thereof.

4. The recombinant bacterium of claim 1, wherein the LpxE polypeptide belongs to EC 3.1.3.-.

5. The recombinant bacterium of claim 1, wherein the LpxE polypeptide is a polypeptide having Lipid A-1 phosphatase activity and comprising an amino acid sequence having 90% or more sequence identity to the amino acid sequence of SEQ ID NO: 9 or SEQ ID NO: 17.

6. The recombinant bacterium of claim 3, wherein the LpxL polypeptide belongs to EC 2.3.1.241 and the LpxM polypeptide belongs to EC 2.3.1.243.

7. The recombinant bacterium of claim 3, wherein the LpxL polypeptide is a polypeptide having lipid A biosynthesis lauroyltransferase activity and comprising an amino acid sequence having 90% or more sequence identity to the amino acid sequence of SEQ ID NO: 1 and the LpxM polypeptide is a polypeptide having lipid A biosynthesis myristoyltransferase activity and comprising 90% or more sequence identity to the amino acid sequence of SEQ ID NO: 5.

8. The recombinant bacterium of claim 1, wherein the bacterium is a Gram-negative bacterium.

9. The recombinant bacterium of claim 1, wherein the bacterium is selected from the group consisting of *Escherichia* genus bacterium, *Shigella* genus bacterium, *Salmonella* genus bacterium, *Campylobacter* genus bacterium, *Neisseria* genus bacterium, *Haemophilus* genus bacterium, *Aeromonas* genus bacterium, *Francisella* genus bacterium, *Yersinia* genus bacterium, *Klebsiella* genus bacterium, *Bordetella* genus bacterium, *Legionella* genus bacterium, *Corynebacterium* genus bacterium, *Citrobacter* genus bacterium, *Chlamydia* genus bacterium, *Brucella* genus bacterium, *Pseudomonas* genus bacterium, *Helicobacter* genus bacterium, *Burkholderia* genus bacterium, *Agrobacterium* genus bacterium, *Chlorobium* genus bacterium, *Rhodospirillum* genus bacterium, *Magnetospirillum* genus bacterium, *Chlorobaculum* genus bacterium, *Pelodictyon* genus bacterium, *Pseudovibro* genus bacterium, *Phaeospirillum* genus bacterium, *Syntrophobacter* genus bacterium, *Bradyrhizobium* genus bacterium, *Porphyromonas* genus bacterium, *Rhizobium* genus bacterium, *Mesorhizobium* genus bacterium, *Vibrio* genus bacterium, *Ralstonia* genus bacterium, *Limnohabitans* genus bacterium, and *Thermodesulfobacterium* genus bacterium.

10. The recombinant bacterium of claim 1, wherein the recombinant bacterium has a disruption in a gene selected from a gene encoding a LpxT polypeptide, a gene encoding a PagP polypeptide, a gene encoding a KdtA polypeptide, or a combination thereof.

11. A method of producing MLA, the method comprising:
culturing the recombinant bacterium of claim 1 to obtain a culture comprising MLA; and
isolating MLA from the culture.

12. The method of claim 11, wherein isolating the MLA from the culture comprises isolating MLA from the recombinant bacterium.

13. The method of claim 11, wherein the culturing comprises culturing in batch, fed-batch, or continuous mode.

14. The method of claim 11, wherein the MLA comprises 1-dephospho-lipid A, 1-dephospho-penta-acylated lipid A, 1-dephospho-tetra-acylated lipid A, or a combination thereof.

* * * * *

SEQUENCE LISTING

```
<160> NUMBER OF SEQ ID NOS: 27

<210> SEQ ID NO 1
<211> LENGTH: 306
<212> TYPE: PRT
<213> ORGANISM: Artificial Sequence
<220> FEATURE:
<223> OTHER INFORMATION: Escherichia coli LpxL polypeptide

<400> SEQUENCE: 1

Met Thr Asn Leu Pro Lys Phe Ser Thr Ala Leu Leu His Pro Arg Tyr
1               5                   10                  15

Trp Leu Thr Trp Leu Gly Ile Gly Val Leu Trp Leu Val Val Gln Leu
            20                  25                  30

Pro Tyr Pro Val Ile Tyr Arg Leu Gly Cys Gly Leu Gly Lys Leu Ala
        35                  40                  45
```

Leu Arg Phe Met Lys Arg Arg Ala Lys Ile Val His Arg Asn Leu Glu
 50                  55                  60

Leu Cys Phe Pro Glu Met Ser Glu Gln Glu Arg Arg Lys Met Val Val
 65                  70                  75                  80

Lys Asn Phe Glu Ser Val Gly Met Gly Leu Met Glu Thr Gly Met Ala
                 85                  90                  95

Trp Phe Trp Pro Asp Arg Arg Ile Ala Arg Trp Thr Glu Val Ile Gly
             100                 105                 110

Met Glu His Ile Arg Asp Val Gln Ala Gln Lys Arg Gly Ile Leu Leu
         115                 120                 125

Val Gly Ile His Phe Leu Thr Leu Glu Leu Gly Ala Arg Gln Phe Gly
     130                 135                 140

Met Gln Glu Pro Gly Ile Gly Val Tyr Arg Pro Asn Asp Asn Pro Leu
145                 150                 155                 160

Ile Asp Trp Leu Gln Thr Trp Gly Arg Leu Arg Ser Asn Lys Ser Met
                165                 170                 175

Leu Asp Arg Lys Asp Leu Lys Gly Met Ile Lys Ala Leu Lys Lys Gly
            180                 185                 190

Glu Val Val Trp Tyr Ala Pro Asp His Asp Tyr Gly Pro Arg Ser Ser
        195                 200                 205

Val Phe Val Pro Leu Phe Ala Val Glu Gln Ala Ala Thr Thr Thr Gly
    210                 215                 220

Thr Trp Met Leu Ala Arg Met Ser Gly Ala Cys Leu Val Pro Phe Val
225                 230                 235                 240

Pro Arg Arg Lys Pro Asp Gly Lys Gly Tyr Gln Leu Ile Met Leu Pro
                245                 250                 255

Pro Glu Cys Ser Pro Pro Leu Asp Asp Ala Glu Thr Thr Ala Ala Trp
            260                 265                 270

Met Asn Lys Val Val Glu Lys Cys Ile Met Met Ala Pro Glu Gln Tyr
        275                 280                 285

Met Trp Leu His Arg Arg Phe Lys Thr Arg Pro Glu Gly Val Pro Ser
    290                 295                 300

Arg Tyr
305

<210> SEQ ID NO 2
<211> LENGTH: 921
<212> TYPE: DNA
<213> ORGANISM: Artificial Sequence
<220> FEATURE:
<223> OTHER INFORMATION: Polynucleotide encoding Escherichia coli LpxL
      polypeptide

<400> SEQUENCE: 2
atgacgaatc tacccaagtt ctccaccgca ctgcttcatc cgcgttattg gttaacctgg      60
ttgggtattg gcgtactttg gttagtcgtg caattgccct accggttat ctaccgcctc      120 ggttgtggat taggaaaact ggcgttacgt tttatgaaac gacgcgcaaa aattgtgcat      180
cgcaacctgg aactgtgctt cccggaaatg agcgaacaag aacgccgtaa aatggtggtg      240
aagaatttcg aatccgttgg catgggcctg atggaaccg gcatggcgtg gttctggccg      300
gaccgccgaa tcgcccgctg gacggaagtg atcggcatgg aacacattcg tgacgtgcag      360
gcgcaaaaac gcggcatcct gttagttggc atccattttc tgacactgga gctgggtgcg      420
cggcagtttg gtatgcagga accgggtatt ggcgtttatc gcccgaacga taatccactg      480
attgactggc tacaaacctg gggccgtttg cgctcaaata aatcgatgct cgaccgcaaa      540

```
gatttaaaag gcatgattaa agccctgaaa aaaggcgaag tggtctggta cgcaccggat    600
catgattacg gcccgcgctc aagcgttttc gtcccgttgt tgccgttga gcaggctgcg    660 accacgaccg gaacctggat gctggcacgg atgtccggcg catgtctggt gcccttcgtt    720
ccacgccgta agccagatgg caaagggtat caattgatta tgctgccgcc agagtgttct    780
ccgccactgg atgatgccga actaccgcc gcgtggatga acaaagtggt cgaaaaatgc    840
atcatgatgg caccagagca gtatatgtgg ttacaccgtc gctttaaaac acgcccggaa    900
ggcgttcctt cacgctatta a                                              921
```

```
<210> SEQ ID NO 3
<211> LENGTH: 48
<212> TYPE: DNA
<213> ORGANISM: Artificial Sequence
<220> FEATURE:
<223> OTHER INFORMATION: LpxL forward primer P1

<400> SEQUENCE: 3
cgcagtctag aaaggagata tattgatgac gaatctaccc aagttctc                 48

<210> SEQ ID NO 4
<211> LENGTH: 67
<212> TYPE: DNA
<213> ORGANISM: Artificial Sequence
<220> FEATURE:
<223> OTHER INFORMATION: LpxL reverse primer P2

<400> SEQUENCE: 4
cgctattatt tttttcgtt tccattggta tatctccttc ttattaatag cgtgaaggaa     60
cgccttc                                                              67

<210> SEQ ID NO 5
<211> LENGTH: 323
<212> TYPE: PRT
<213> ORGANISM: Artificial Sequence
<220> FEATURE:
<223> OTHER INFORMATION: Escherichia coli LpxM polypeptide

<400> SEQUENCE: 5
```

Met Glu Thr Lys Lys Asn Asn Ser Glu Tyr Ile Pro Glu Phe Asp Lys
 1               5                  10                  15

Ser Phe Arg His Pro Arg Tyr Trp Gly Ala Trp Leu Gly Val Ala Ala
                20                  25                  30

Met Ala Gly Ile Ala Leu Thr Pro Pro Lys Phe Arg Asp Pro Ile Leu
            35                  40                  45

Ala Arg Leu Gly Arg Phe Ala Gly Arg Leu Gly Lys Ser Ser Arg Arg
        50                  55                  60

Arg Ala Leu Ile Asn Leu Ser Leu Cys Phe Pro Glu Arg Ser Glu Ala
65                  70                  75                  80

Glu Arg Glu Ala Ile Val Asp Glu Met Phe Ala Thr Ala Pro Gln Ala
                85                  90                  95

Met Ala Met Met Ala Glu Leu Ala Ile Arg Gly Pro Glu Lys Ile Gln
            100                 105                 110

Pro Arg Val Asp Trp Gln Gly Leu Glu Ile Ile Glu Glu Met Arg Arg
        115                 120                 125

Asn Asn Glu Lys Val Ile Phe Leu Val Pro His Gly Trp Ala Val Asp
    130                 135                 140

Ile Pro Ala Met Leu Met Ala Ser Gln Gly Gln Lys Met Ala Ala Met

```
            145                 150                 155                 160
        Phe His Asn Gln Gly Asn Pro Val Phe Asp Tyr Val Trp Asn Thr Val
                        165                 170                 175

Arg Arg Arg Phe Gly Arg Leu His Ala Arg Asn Asp Gly Ile Lys
                        180                 185                 190

Pro Phe Ile Gln Ser Val Arg Gln Gly Tyr Trp Gly Tyr Leu Pro
                        195                 200                 205

Asp Gln Asp His Gly Pro Glu His Ser Glu Phe Val Asp Phe Phe Ala
                        210                 215                 220

Thr Tyr Lys Ala Thr Leu Pro Ala Ile Gly Arg Leu Met Lys Val Cys
        225                 230                 235                 240

Arg Ala Arg Val Val Pro Leu Phe Pro Ile Tyr Asp Gly Lys Thr His
                        245                 250                 255

Arg Leu Thr Ile Gln Val Arg Pro Pro Met Asp Asp Leu Leu Glu Ala
                        260                 265                 270

Asp Asp His Thr Ile Ala Arg Arg Met Asn Glu Glu Val Glu Ile Phe
                        275                 280                 285

Val Gly Pro Arg Pro Glu Gln Tyr Thr Trp Ile Leu Lys Leu Leu Lys
                        290                 295                 300

Thr Arg Lys Pro Gly Glu Ile Gln Pro Tyr Lys Arg Lys Asp Leu Tyr
        305                 310                 315                 320

Pro Ile Lys

<210> SEQ ID NO 6
<211> LENGTH: 972
<212> TYPE: DNA
<213> ORGANISM: Artificial Sequence
<220> FEATURE:
<223> OTHER INFORMATION: Polynucleotide encoding Escherichia coli LpxM
      polypeptide

<400> SEQUENCE: 6
atggaaacga aaaaaaataa tagcgaatac attcctgagt ttgataaatc ctttcgccac      60
ccgcgctact gggagcatg gctgggcgta gcagcgatgg cgggtatcgc tttaacgccg     120
ccaaagttcc gtgatccat tctggcacgg ctggacgtt tgccggacg actgggaaaa      180 agctcacgcc gtcgtgcgtt aatcaatctg tcgctctgct ttccagaacg tagtgaagct     240
gaacgcgaag cgattgttga tgagatgttt gccaccgcgc cgcaagcgat ggcaatgatg     300
gctgagttgg caatacgcgg gccggagaaa attcagccgc gcgttgactg caagggctg      360 gagatcatcg aagagatgcg gcgtaataac gagaaagtta tctttctggt gccgcacggt     420
tgggccgtcg atattcctgc catgctgatg gcctcgcaag gcagaaaat ggcagcgatg     480 ttccataatc agggcaaccc ggttttttgat tatgtctgga cacggtgcg tcgtcgcttt      540 ggcggtcgtc tgcatgcgag aaatgacggt attaaaccat tcatccagtc ggtacgtcag     600
gggtactggg gatattattt acccgatcag gatcatggcc agagcacag cgaatttgtg     660 gatttctttg ccacctataa agcgacgttg cccgcgattg gtcgtttgat gaaagtgtgc     720
cgtgcgcgcg ttgtaccgct gtttccgatt tatgatggca agacgcatcg tctgacgatt      780
caggtgcgcc caccgatgga tgatctgtta gaggcggatg atcatacgat tgcgcggcgg     840
atgaatgaag aagtcgagat ttttgttggt ccgcgaccag aacaatacac ctggatacta     900
aaattgctga aactcgcaa accgggcgaa atccagccgt ataagcgcaa agatctttat     960
cccatcaaat aa                                                         972
```

<210> SEQ ID NO 7
<211> LENGTH: 67
<212> TYPE: DNA
<213> ORGANISM: Artificial Sequence
<220> FEATURE:
<223> OTHER INFORMATION: LpxM forward primer P3

<400> SEQUENCE: 7

```
gaaggcgttc cttcacgcta ttaataagaa ggagatatac caatggaaac gaaaaaaat      60 aatagcg                                                               67
```

<210> SEQ ID NO 8
<211> LENGTH: 37
<212> TYPE: DNA
<213> ORGANISM: Artificial Sequence
<220> FEATURE:
<223> OTHER INFORMATION: LpxM reverse primer P3

<400> SEQUENCE: 8

```
gcagaagctt ttatttgatg ggataaagat ctttgcg                              37
```

<210> SEQ ID NO 9
<211> LENGTH: 174
<212> TYPE: PRT
<213> ORGANISM: Artificial Sequence
<220> FEATURE:
<223> OTHER INFORMATION: Aquifex aeolicus LpxE polypeptide

<400> SEQUENCE: 9

```
Met Val Ile Glu Asp Phe Ala Leu Asn Leu Glu Leu Phe Arg Leu Ile
1               5                   10                  15

Asn Asn Ala Arg His Pro Leu Leu Asp Val Phe Phe Thr His Phe Ala
            20                  25                  30

Tyr Leu Gly Ser Gly Tyr Val Leu Phe Pro Leu Leu Ile Phe Leu Phe
        35                  40                  45

Ile Phe Arg Lys Glu Lys Val Lys Pro Leu Ile Leu Ala Ile Ile Leu
    50                  55                  60

Glu Thr Val Leu Val Ile Ser Leu Lys Thr Phe Phe Asn Gln Pro Arg
65                  70                  75                  80

Pro Ala Ile Leu Leu Glu Asp Val Asn Leu Leu Phe Pro Leu His Trp
                85                  90                  95

Arg Ser Phe Pro Ser Gly Asp Thr Ala Met Ala Phe Thr Ile Ala Thr
            100                 105                 110

Val Leu Ser His Gly Glu Lys Leu His Ile Lys Ala Ile Leu Phe Leu
        115                 120                 125

Tyr Ala Phe Leu Ile Gly Tyr Glu Arg Ile Tyr Ala Gly Val His Phe
    130                 135                 140

Pro Leu Asp Val Phe Val Gly Ala Leu Ile Gly Ile Ile Cys Gly Ile
145                 150                 155                 160

Ile Ser Leu Lys Tyr Ser Lys Gly Gly Val Tyr Glu Arg Asn
                165                 170
```

<210> SEQ ID NO 10
<211> LENGTH: 525
<212> TYPE: DNA
<213> ORGANISM: Artificial Sequence
<220> FEATURE:
<223> OTHER INFORMATION: Polynucleotide encoding Aquifex aeolicus LpxE
      polypeptide

<400> SEQUENCE: 10

-continued

```
atggtaatag aagactttgc tctaaacctt gaacttttc gtttgataaa caatgcgagg      60
catccacttc tggacgtttt ctttactcac tttgcttacc tcggttcggg ctatgtactg     120
tttcctttat taatctttct ttttattttc agaaaggaaa aagtaaagcc tttgatttta    180
gcgataattt tggaaacagt tttagtgatc tctctaaaaa catttttcaa ccagccgaga    240
cctgcaattt tactcgagga tgtaaactta cttttccctt tacactggcg ttcctttccc    300
tcaggagaca ccgctatggc ttttacgata gcaactgtac tgtcacatgg tgaaaaactc    360
catataaagg caatactctt cttatacgct ttcctaatag ggtatgagag gatttacgcg    420
ggtgttcact ttcctctgga cgttttgta ggagctctga ttggaattat ttgcggtatt     480
atttctttaa aatattccaa gggaggtgtg tatgagagaa attag                    525
```

<210> SEQ ID NO 11
<211> LENGTH: 39
<212> TYPE: DNA
<213> ORGANISM: Artificial Sequence
<220> FEATURE:
<223> OTHER INFORMATION: AaLpxE forward primer

<400> SEQUENCE: 11

```
gcatgccata tgatggtaat agaagacttt gctctaaac                            39
```

<210> SEQ ID NO 12
<211> LENGTH: 36
<212> TYPE: DNA
<213> ORGANISM: Artificial Sequence
<220> FEATURE:
<223> OTHER INFORMATION: AaLpxE reverse primer

<400> SEQUENCE: 12

```
attagcctcg agatttctct catacacacc tccctt                               36
```

<210> SEQ ID NO 13
<211> LENGTH: 20
<212> TYPE: DNA
<213> ORGANISM: Artificial Sequence
<220> FEATURE:
<223> OTHER INFORMATION: AaLpxE forward primer

<400> SEQUENCE: 13

```
taatacgact cactataggg                                                 20
```

<210> SEQ ID NO 14
<211> LENGTH: 35
<212> TYPE: DNA
<213> ORGANISM: Artificial Sequence
<220> FEATURE:
<223> OTHER INFORMATION: AaLpxE reverse primer

<400> SEQUENCE: 14

```
gcagaagctt ctaatttctc tcatacacac ctccc                                35
```

<210> SEQ ID NO 15
<211> LENGTH: 573
<212> TYPE: DNA
<213> ORGANISM: Artificial Sequence
<220> FEATURE:
<223> OTHER INFORMATION: Helicobactor pylori LpxE sequence

<400> SEQUENCE: 15

```
atgaaaaaat tcttatttaa acaaaaattt tgtgaaagcc tgcccaaaag ctttctaaa      60
```

```
actttgttag cgctcagttt gggcttgatt ttattaggca ttttgcgcc tttccctaaa      120 gtccctaaac agcctagcgt gcctttaatg tttcatttca ccgagcatta tgcgcgcttt      180
atccctacga ttttatctgt ggcgattccc ttaatccaaa gagatgcggt agggcttttt      240
caagtcgcta acgcttctat cgctacaacc cttctcacgc acaccaccaa aagagcctta      300
aaccatgtaa caatcaacga tcagcgtttg ggcgagcgcc cttatggagg taatttcaac      360
atgccaagcg ggcattcgtc tatggtgggt ttggcggtgg cgtttttaat gcgccgctat      420
tcttttaaaa aatactttg gctcttgccc ctagtccctt tgaccatgct cgctcgcatt      480
tatttagaca tgcacaccat ggcgcggtg ctgaccgggc ttggcgttgg aatgttgtgc      540
gtaagccttt ttacaagccc caaaaagcct taa                                  573
```

<210> SEQ ID NO 16
<211> LENGTH: 573
<212> TYPE: DNA
<213> ORGANISM: Artificial Sequence
<220> FEATURE:
<223> OTHER INFORMATION: Mutated Helicobactor pylori LpxE sequence
      (A49T, G50C, and C51G)

<400> SEQUENCE: 16

```
atgaaaaaat tcttatttaa acaaaaattt tgtgaaagcc tgcccaaatc gtttctaaa       60 actttgttag cgctcagttt gggcttgatt ttattaggca ttttgcgcc tttccctaaa      120 gtccctaaac agcctagcgt gcctttaatg tttcatttca ccgagcatta tgcgcgcttt      180
atccctacga ttttatctgt ggcgattccc ttaatccaaa gagatgcggt agggcttttt      240
caagtcgcta acgcttctat cgctacaacc cttctcacgc acaccaccaa aagagcctta      300
aaccatgtaa caatcaacga tcagcgtttg ggcgagcgcc cttatggagg taatttcaac      360
atgccaagcg ggcattcgtc tatggtgggt ttggcggtgg cgtttttaat gcgccgctat      420
tcttttaaaa aatactttg gctcttgccc ctagtccctt tgaccatgct cgctcgcatt      480
tatttagaca tgcacaccat ggcgcggtg ctgaccgggc ttggcgttgg aatgttgtgc      540
gtaagccttt ttacaagccc caaaaagcct taa                                  573
```

<210> SEQ ID NO 17
<211> LENGTH: 190
<212> TYPE: PRT
<213> ORGANISM: Artificial Sequence
<220> FEATURE:
<223> OTHER INFORMATION: Helicobactor pylori LpxE Amino acid sequence

<400> SEQUENCE: 17

```
Met Lys Lys Phe Leu Phe Lys Gln Lys Phe Cys Glu Ser Leu Pro Lys
1               5                   10                  15

Ser Phe Ser Lys Thr Leu Leu Ala Leu Ser Leu Gly Leu Ile Leu Leu
            20                  25                  30

Gly Ile Phe Ala Pro Phe Pro Lys Val Pro Lys Gln Pro Ser Val Pro
        35                  40                  45

Leu Met Phe His Phe Thr Glu His Tyr Ala Arg Phe Ile Pro Thr Ile
    50                  55                  60

Leu Ser Val Ala Ile Pro Leu Ile Gln Arg Asp Ala Val Gly Leu Phe
65                  70                  75                  80

Gln Val Ala Asn Ala Ser Ile Ala Thr Thr Leu Leu Thr His Thr Thr
                85                  90                  95

Lys Arg Ala Leu Asn His Val Thr Ile Asn Asp Gln Arg Leu Gly Glu
            100                 105                 110
```

```
Arg Pro Tyr Gly Gly Asn Phe Asn Met Pro Ser Gly His Ser Ser Met
        115                 120                 125

Val Gly Leu Ala Val Ala Phe Leu Met Arg Arg Tyr Ser Phe Lys Lys
    130                 135                 140

Tyr Phe Trp Leu Leu Pro Leu Val Pro Leu Thr Met Leu Ala Arg Ile
145                 150                 155                 160

Tyr Leu Asp Met His Thr Ile Gly Ala Val Leu Thr Gly Leu Gly Val
                165                 170                 175

Gly Met Leu Cys Val Ser Leu Phe Thr Ser Pro Lys Lys Pro
                180                 185                 190
```

<210> SEQ ID NO 18
<211> LENGTH: 55
<212> TYPE: DNA
<213> ORGANISM: Artificial Sequence
<220> FEATURE:
<223> OTHER INFORMATION: HpLpxE forward primer

<400> SEQUENCE: 18
gatcctctag aaaggagata tattgatgaa aaaattctta tttaaacaaa aattt        55

<210> SEQ ID NO 19
<211> LENGTH: 29
<212> TYPE: DNA
<213> ORGANISM: Artificial Sequence
<220> FEATURE:
<223> OTHER INFORMATION: HpLpxE reverse primer

<400> SEQUENCE: 19
agctacaagc ttttaaggct ttttggggc                                     29

<210> SEQ ID NO 20
<211> LENGTH: 237
<212> TYPE: PRT
<213> ORGANISM: Artificial Sequence
<220> FEATURE:
<223> OTHER INFORMATION: Escherichia coli LpxT polypeptide

<400> SEQUENCE: 20

```
Met Ile Lys Asn Leu Pro Gln Ile Val Leu Asn Ile Val Gly Leu
1               5                   10                  15

Ala Leu Phe Leu Ser Trp Tyr Ile Pro Val Asn His Gly Phe Trp Leu
                20                  25                  30

Pro Ile Asp Ala Asp Ile Phe Tyr Phe Phe Asn Gln Lys Leu Val Glu
            35                  40                  45

Ser Lys Ala Phe Leu Trp Leu Val Ala Leu Thr Asn Asn Arg Ala Phe
    50                  55                  60

Asp Gly Cys Ser Leu Leu Ala Met Gly Met Leu Met Leu Ser Phe Trp
65                  70                  75                  80

Leu Lys Glu Asn Ala Pro Gly Arg Arg Arg Ile Val Ile Ile Gly Leu
                85                  90                  95

Val Met Leu Leu Thr Ala Val Val Leu Asn Gln Leu Gly Gln Ala Leu
                100                 105                 110

Ile Pro Val Lys Arg Ala Ser Pro Thr Leu Thr Phe Thr Asp Ile Asn
            115                 120                 125

Arg Val Ser Glu Leu Leu Ser Val Pro Thr Lys Asp Ala Ser Arg Asp
    130                 135                 140

Ser Phe Pro Gly Asp His Gly Met Met Leu Leu Ile Phe Ser Ala Phe
145                 150                 155                 160
```

```
Met Trp Arg Tyr Phe Gly Lys Val Ala Gly Leu Ile Ala Leu Ile Ile
            165                 170                 175

Phe Val Val Phe Ala Phe Pro Arg Val Met Ile Gly Ala His Trp Phe
        180                 185                 190

Thr Asp Ile Ile Val Gly Ser Met Thr Val Ile Leu Ile Gly Leu Pro
        195                 200                 205

Trp Val Leu Leu Thr Pro Leu Ser Asp Arg Leu Ile Thr Phe Phe Asp
    210                 215                 220

Lys Ser Leu Pro Gly Lys Asn Lys His Phe Gln Asn Lys
225                 230                 235

<210> SEQ ID NO 21
<211> LENGTH: 714
<212> TYPE: DNA
<213> ORGANISM: Artificial Sequence
<220> FEATURE:
<223> OTHER INFORMATION: Polynucleotide encoding Escherichia coli LpxT
      polypeptide

<400> SEQUENCE: 21
atgattaaaa atttgccgca aatagtgttg ttgaatattg tcggcctcgc gctgtttctt      60
tcctggtata tccccgttaa tcatggattc tggttgccga ttgatgcgga tatttttttat    120 ttctttaatc agaaactggt cgaaagtaag gccttttttgt ggctggttgc attgaccaac    180
aatcgcgcct tcgacggttg ttcactgctg gcgatgggta tgttgatgct gagtttctgg    240
ctgaaagaaa acgcccctgg cagacgacgt atcgtgatta ttggtctggt catgctatta    300
actgcagtgg tattaaacca gctgggtcag gcattaattc ctgtaaaacg ggccagccca    360
acattgactt ttaccgatat taaccgcgtc agcgaactgc tctctgttcc cacgaaagat    420
gcctcacgag atagctttcc cggcgatcac ggcatgatgc tgcttatttt ttcggcattc    480
atgtggcgtt atttcggcaa agttgcaggc cttatcgccc ttattatttt tgtggttttt    540
gcatttccca gagtaatgat tggcgcacac tggtttactg acatcattgt cggttcgatg    600
accgtgatat tgatcggttt gccctgggtg ttgctgacgc cattaagtga tcgattaatc    660
accttttttg acaaatcact accaggaaaa aacaaacatt tccaaaacaa ataa           714

<210> SEQ ID NO 22
<211> LENGTH: 425
<212> TYPE: PRT
<213> ORGANISM: Artificial Sequence
<220> FEATURE:
<223> OTHER INFORMATION: Escherichia coli KdtA polypeptide

<400> SEQUENCE: 22

Met Leu Glu Leu Leu Tyr Thr Ala Leu Leu Tyr Leu Ile Gln Pro Leu
1               5                   10                  15

Ile Trp Ile Arg Leu Trp Val Arg Gly Arg Lys Ala Pro Ala Tyr Arg
            20                  25                  30

Lys Arg Trp Gly Glu Arg Tyr Gly Phe Tyr Arg His Pro Leu Lys Pro
        35                  40                  45

Gly Gly Ile Met Leu His Ser Val Ser Val Gly Glu Thr Leu Ala Ala
    50                  55                  60

Ile Pro Leu Val Arg Ala Leu Arg His Arg Tyr Pro Asp Leu Pro Ile
65                  70                  75                  80

Thr Val Thr Thr Met Thr Pro Thr Gly Ser Glu Arg Val Gln Ser Ala
                85                  90                  95
```

```
Phe Gly Lys Asp Val Gln His Val Tyr Leu Pro Tyr Asp Leu Pro Asp
                100                 105                 110

Ala Leu Asn Arg Phe Leu Asn Lys Val Asp Pro Lys Leu Val Leu Ile
            115                 120                 125

Met Glu Thr Glu Leu Trp Pro Asn Leu Ile Ala Ala Leu His Lys Arg
        130                 135                 140

Lys Ile Pro Leu Val Ile Ala Asn Ala Arg Leu Ser Ala Arg Ser Ala
145                 150                 155                 160

Ala Gly Tyr Ala Lys Leu Gly Lys Phe Val Arg Arg Leu Leu Arg Arg
                165                 170                 175

Ile Thr Leu Ile Ala Ala Gln Asn Glu Glu Asp Gly Ala Arg Phe Val
            180                 185                 190

Ala Leu Gly Ala Lys Asn Asn Gln Val Thr Val Thr Gly Ser Leu Lys
        195                 200                 205

Phe Asp Ile Ser Val Thr Pro Gln Leu Ala Ala Lys Ala Val Thr Leu
    210                 215                 220

Arg Arg Gln Trp Ala Pro His Arg Pro Val Trp Ile Ala Thr Ser Thr
225                 230                 235                 240

His Glu Gly Glu Ser Val Val Ile Ala His Gln Ala Leu Leu
                245                 250                 255

Gln Gln Phe Pro Asn Leu Leu Leu Ile Leu Val Pro Arg His Pro Glu
            260                 265                 270

Arg Phe Pro Asp Ala Ile Asn Leu Val Arg Gln Ala Gly Leu Ser Tyr
        275                 280                 285

Ile Thr Arg Ser Ser Gly Glu Val Pro Ser Thr Ser Thr Gln Val Val
    290                 295                 300

Val Gly Asp Thr Met Gly Glu Leu Met Leu Leu Tyr Gly Ile Ala Asp
305                 310                 315                 320

Leu Ala Phe Val Gly Gly Ser Leu Val Glu Arg Gly Gly His Asn Pro
                325                 330                 335

Leu Glu Ala Ala Ala His Ala Ile Pro Val Leu Met Gly Pro His Thr
            340                 345                 350

Phe Asn Phe Lys Asp Ile Cys Ala Arg Leu Glu Gln Ala Ser Gly Leu
        355                 360                 365

Ile Thr Val Thr Asp Ala Thr Thr Leu Ala Lys Glu Val Ser Ser Leu
    370                 375                 380

Leu Thr Asp Ala Asp Tyr Arg Ser Phe Tyr Gly Arg His Ala Val Glu
385                 390                 395                 400

Val Leu Tyr Gln Asn Gln Gly Ala Leu Gln Arg Leu Leu Gln Leu Leu
                405                 410                 415

Glu Pro Tyr Leu Pro Pro Lys Thr His
            420                 425

<210> SEQ ID NO 23
<211> LENGTH: 1278
<212> TYPE: DNA
<213> ORGANISM: Artificial Sequence
<220> FEATURE:
<223> OTHER INFORMATION: Polynucleotide encoding Escherichia coli KdtA
      polypeptide

<400> SEQUENCE: 23
atgctcgaat tgctttacac cgcccttctc taccttattc agccgctgat ctggatacgg      60
ctctgggtgc gcggacgtaa ggctccggcc tatcgaaaac gctggggtga acgttacggt     120
ttttaccgcc atccgctaaa accaggcggc attatgctgc actccgtctc cgtcggtgaa     180
```

```
actctggcgg caatcccgtt ggtgcgcgcg ctgcgtcatc gttatcctga tttaccgatt    240
accgtaacaa ccatgacgcc aaccggttcg gagcgcgtac aatcggcttt cgggaaggat    300
gttcagcacg tttatctgcc gtatgatctg cccgatgcac tcaaccgttt cctgaataaa    360
gtcgacccta aactggtgtt gattatgaaa accgaactat ggcctaacct gattgcggcg    420
ctacataaac gtaaaattcc gctggtgatc gctaacgcgc gactctctgc ccgctcggcc    480
gcaggttatg ccaaactggg taaattcgtc cgtcgcttgc tgcgtcgtat tacgctgatt    540
gctgcgcaaa atgaagaaga tggtgcacgt tttgtggcgc tgggcgcaaa aaataatcag    600
gtgaccgtta ccggtagcct gaaattcgat atttctgtaa cgccgcagtt ggctgctaaa    660
gccgtgacgc tgcgccgcca gtgggcacca caccgcccgg tatggattgc caccagcact    720
cacgaaggcg aagagagtgt ggtgatcgcc gcacatcagg cattgttaca gcaattcccg    780
aatttattgc tcatcctggt accccgtcat ccggaacgct cccggatgc gattaacctt    840 gtccgccagg ctggactaag ctatatcaca cgctcttcag gggaagtccc ctccaccagc    900
acgcaggttg tggttggcga tacgatgggc gagttgatgt tactgtatgg cattgccgat    960
ctcgcctttg ttggcggttc actggttgaa cgtggtgggc ataatccgct ggaagctgcc   1020
gcacacgcta ttccggtatt gatggggccg catactttta actttaaaga catttgcgcg   1080
cggctggagc aggcaagcgg gctgattacc gttaccgatg ccactacgct tgcaaaagag   1140
gtttcctctt tactcaccga cgccgattac cgtagtttct atggccgtca tgccgttgaa   1200
gtactgtatc aaaaccaggg cgcgctacag cgtctgcttc aactgctgga accttacctg   1260
ccaccgaaaa cgcattga                                                 1278
```

<210> SEQ ID NO 24
<211> LENGTH: 239
<212> TYPE: PRT
<213> ORGANISM: Artificial Sequence
<220> FEATURE:
<223> OTHER INFORMATION: Francisella novicida LpxE polypeptide

<400> SEQUENCE: 24

```
Met Leu Lys Gln Thr Leu Gln Thr Asn Phe Gln Gly Phe Lys Asp Ile
1               5                   10                  15

Phe Lys Lys Pro Lys Leu His Asn His Lys Leu Pro Arg Tyr Leu Gln
                20                  25                  30

Leu Lys Tyr Thr Phe Ile Pro Leu Leu Ile Leu Val Ile Phe Ala Tyr
            35                  40                  45

Tyr Asn Leu Asp Thr Pro Val Glu Asn Tyr Ile Lys His Ser Met Pro
50                  55                  60

Asn Ile Val Gly Val Ile Phe Gly Lys Ile Thr Asp Val Gly Lys Ala
65                  70                  75                  80

Glu Tyr Ile Leu Ile Ile Cys Gly Val Ile Val Leu Ala Arg Leu Phe
                85                  90                  95

Thr Asp Ser Gln Lys Leu Ser Ala Asn Thr Arg Ala Met Phe Asp Lys
            100                 105                 110

Val Ser Ala Tyr Ala Gly Phe Ile Leu Ala Thr Val Ala Ile Ser Gly
        115                 120                 125

Ile Leu Gly Gln Ile Leu Lys Met Ile Ile Gly Arg Ala Arg Pro Lys
    130                 135                 140

Phe Phe Leu Glu Tyr Gly Ser His Tyr Phe Gln His Phe His Ala Pro
145                 150                 155                 160
```

-continued

Gly Tyr Asp Phe Ala Ser Met Pro Ser Gly His Ser Ile Thr Val Gly
            165                 170                 175

Ala Met Phe Ile Ala Phe Phe Tyr Ile Phe Pro Lys Leu Arg Tyr Phe
        180                 185                 190

Trp Tyr Leu Leu Ile Val Val Phe Ala Gly Ser Arg Ile Met Val Gly
            195                 200                 205

Ser His Tyr Pro Ser Asp Val Ile Phe Gly Val Ala Phe Gly Cys Tyr
        210                 215                 220

Cys Thr Ala Tyr Ile Tyr Tyr Trp Met Arg Asn Arg Glu Ile Ile
225                 230                 235

<210> SEQ ID NO 25
<211> LENGTH: 720
<212> TYPE: DNA
<213> ORGANISM: Artificial Sequence
<220> FEATURE:
<223> OTHER INFORMATION: Polynucleotide encoding Francisella novicida
      LpxE polypeptide

<400> SEQUENCE: 25
atgctcaaac agacattaca aacaaacttt caaggttta aagatatttt taaaaaacca    60
aaactacaca atcataaatt gcctagatat ctacagttga atatacgtt tataccatta   120 ttaattttgg taattttgc atactataac ttagataccc cagttgagaa ctatatcaag   180
cattctatgc caaatattgt tggtgtaatt tttggtaaaa taactgatgt tggtaaggcc   240
gagtatattt tgataatttg cggtgtgata gtgttagcgc gtttatttac agatagccaa   300
aaattatctg ctaatactag agctatgttt gacaaggtgt cggcatatgc gggttttatc   360
ttagcaactg tagctattag tggtattttg ggacaaatac tcaagatgat aataggtaga   420
gcgcgtccta gttttttctt ggaatatggt tcgcattatt ccaacatttt tcatgcacct   480
ggatatgatt ttgcaagtat gccgtcaggg cactcaatca cagttggagc aatgttata   540 gcattttttt atattttccc taagctaaga tattttggt atttgctgat agtggtattt   600
gctgggagta gaattatggt tggttcacat tatcctagtg atgtaatttt tggcgttgct   660
tttggttgtt actgtacagc atatatctac tattggatga aaatagaga gattatttag   720

<210> SEQ ID NO 26
<211> LENGTH: 186
<212> TYPE: PRT
<213> ORGANISM: Artificial Sequence
<220> FEATURE:
<223> OTHER INFORMATION: Escherichia coli PagP polypeptide

<400> SEQUENCE: 26

Met Asn Val Ser Lys Tyr Val Ala Ile Phe Ser Phe Val Phe Ile Gln
1               5                   10                  15

Leu Ile Ser Val Gly Lys Val Phe Ala Asn Ala Asp Glu Trp Met Thr
            20                  25                  30

Thr Phe Arg Glu Asn Ile Ala Gln Thr Trp Gln Gln Pro Glu His Tyr
        35                  40                  45

Asp Leu Tyr Ile Pro Ala Ile Thr Trp His Ala Arg Phe Ala Tyr Asp
    50                  55                  60

Lys Glu Lys Thr Asp Arg Tyr Asn Glu Arg Pro Trp Gly Gly Gly Phe
65                  70                  75                  80

Gly Leu Ser Arg Trp Asp Glu Lys Gly Asn Trp His Gly Leu Tyr Ala
                85                  90                  95

Met Ala Phe Lys Asp Ser Trp Asn Lys Trp Glu Pro Ile Ala Gly Tyr

```
                        100                 105                 110
Gly Trp Glu Ser Thr Trp Arg Pro Leu Ala Asp Glu Asn Phe His Leu
            115                 120                 125

Gly Leu Gly Phe Thr Ala Gly Val Thr Ala Arg Asp Asn Trp Asn Tyr
    130                 135                 140

Ile Pro Leu Pro Val Leu Leu Pro Leu Ala Ser Val Gly Tyr Gly Pro
145                 150                 155                 160

Val Thr Phe Gln Met Thr Tyr Ile Pro Gly Thr Tyr Asn Asn Gly Asn
                165                 170                 175

Val Tyr Phe Ala Trp Met Arg Phe Gln Phe
            180                 185

<210> SEQ ID NO 27
<211> LENGTH: 561
<212> TYPE: DNA
<213> ORGANISM: Artificial Sequence
<220> FEATURE:
<223> OTHER INFORMATION: Polynucleotide encoding Escherichia coli pagP
      polypeptide

<400> SEQUENCE: 27
atgaacgtga gtaaatatgt cgctatcttt tcctttgttt ttattcagtt aatcagcgtt      60
ggtaaagttt ttgctaacgc agatgagtgg atgacaacgt ttagagaaaa tattgcacaa     120
acctggcaac agcctgaaca ttatgattta tatattcctg ccatcacctg gcatgcacgt     180
ttcgcttacg acaaagaaaa aaccgatcgc tataacgagc gaccgtgggg tggcggtttt     240
ggcctgtcgc gttgggatga aaaaggaaac tggcatggcc tgtatgccat ggcatttaag     300
gactcgtgga acaaatggga accgattgcc ggatacggat gggaaagtac ctggcgaccg     360
ctggcggatg aaaattttca tttaggtctg ggattcaccg ctggcgtaac ggcacgcgat     420
aactggaatt acatccctct cccggttcta ctgccattgg cctccgtggg ttatggccca     480 gtgactttc agatgaccta cattccgggt acctacaaca atggcaatgt gtactttgcc      540
tggatgcgct ttcagttttg a                                               561
```